(12) United States Patent
Vrinten et al.

(10) Patent No.: US 8,088,978 B2
(45) Date of Patent: Jan. 3, 2012

(54) OMEGA-3 FATTY ACID DESATURASE FAMILY MEMBERS AND USES THEREOF

(75) Inventors: Patricia Vrinten, Saskatoon (CA); Xiao Qiu, Saskatoon (CA)

(73) Assignee: Bioriginal Food & Science Corp., Saskatoon (CA)

( * ) Notice: Subject to any disclaimer, the term of this patent is extended or adjusted under 35 U.S.C. 154(b) by 903 days.

(21) Appl. No.: 11/883,134

(22) PCT Filed: Feb. 7, 2006

(86) PCT No.: PCT/CA2006/000156
§ 371 (c)(1),
(2), (4) Date: May 6, 2008

(87) PCT Pub. No.: WO2006/084352
PCT Pub. Date: Aug. 17, 2006

(65) Prior Publication Data
US 2009/0055973 A1    Feb. 26, 2009

Related U.S. Application Data

(60) Provisional application No. 60/651,568, filed on Feb. 9, 2005.

(51) Int. Cl.
*A01H 5/00* (2006.01)
*C12N 15/82* (2006.01)
*C07H 21/04* (2006.01)

(52) U.S. Cl. ........ 800/298; 435/419; 536/23.2; 800/281

(58) Field of Classification Search .................. None
See application file for complete search history.

(56) References Cited

FOREIGN PATENT DOCUMENTS

| | | |
|---|---|---|
| JP | 9065882 A | 3/1997 |
| WO | WO-94/18337 A1 | 8/1994 |
| WO | WO-98/18948 A1 | 5/1998 |
| WO | WO-01/16340 A1 | 3/2001 |
| WO | WO-01/25453 A2 | 4/2001 |
| WO | WO-02/102970 A2 | 12/2002 |
| WO | WO-2005/108568 A1 | 11/2005 |

OTHER PUBLICATIONS

Kim et al, Plant Mol Biol 24:105-117, 1994.*
Rowland, G. G., "An EMS-Induced Low-Linolenic-Acid Mutant in McGregor Flax (*Linum usitatissimum* L.)", Canadian Journal of Plant Science, 1991, vol. 71, No. 2, pp. 393-396.
Vrinten, Patricia et al., "Two FAD3 Desaturase Genes Control the Level of Linolenic Acid in Flax Seed," *Plant Physiology*, vol. 139:79-87 (2005).
International Search Report for Application No. PCT/CA2006/000156, dated May 8, 2006.
Written Opinion for Application No. PCT/CA2006/000156, dated May 8, 2006.

* cited by examiner

*Primary Examiner* — Elizabeth McElwain
(74) *Attorney, Agent, or Firm* — Connolly Bove Lodge & Hutz, LLP

(57) ABSTRACT

The present invention relates to the isolation of a second omega-3 fatty acid desaturase (FAD3) gene in flax (*Linum usitatissimum*) and its promoter region, as well as the identification of FAD3 mutant alleles, and the development of markers for wild type and mutated alleles. The FAD3 genes encode the enzymes which control omega-3 fatty acid desaturation and, thus, the levels of linolenic acid (18:3(n-3)). Accordingly, the molecules of the present invention can be utilized, for example, to develop markers for the mutations in flax FAD3 genes and for seed-specific modification of fatty acid and protein compositions in plant seeds.

22 Claims, 3 Drawing Sheets

Figure 2

| CLONE | FED | Area % from GC analysis | | | | | |
|---|---|---|---|---|---|---|---|
| | | C16:0 | C16:1 (n-7) | C18:0 | C18:1(n-9) | C18:2(n-6) | C18:3(n-3) |
| Vector (pYES) | None | 18.24 | 41.77 | 5.44 | 23.76 | ND | ND |
| | 18:2(n-6) | 20.40 | 22.68 | 6.25 | 14.10 | 28.47 | ND |
| pYES/NormLuFADA | None | 18.21 | 41.86 | 5.84 | 23.38 | ND | ND |
| | 18:2(n-6) | 19.96 | 21.54 | 6.15 | 12.87 | 30.46 | 1.28 |
| pYES/NormLuFADB | None | 18.38 | 41.37 | 5.72 | 23.49 | ND | ND |
| | 18:2(n-6) | 19.74 | 22.34 | 5.80 | 13.02 | 28.91 | 2.02 |
| pYES/SolinLuFADA | None | 18.78 | 42.75 | 5.76 | 23.72 | ND | ND |
| | 18:2(n-6) | 19.94 | 23.11 | 6.19 | 13.97 | 28.44 | ND |
| pYES/SolinLuFADB | None | 18.94 | 41.83 | 5.51 | 23.01 | ND | ND |
| | 18:2(n-6) | 19.99 | 21.64 | 5.54 | 12.28 | 31.52 | ND |

LuFAD3A  LuFAD3B

SEQUENCE LISTING

<160> NUMBER OF SEQ ID NOS: 39

<210> SEQ ID NO 1
<211> LENGTH: 1536
<212> TYPE: DNA
<213> ORGANISM: Linum usitatissimum

<400> SEQUENCE: 1

```
tgcagattat agtgacttca aaactgtggc tctgcaggac caaactatga gccctccaaa      60
ctcaatgagt cccaccacca acggcaatgg tgtggctatg aatggggcga agaagcagct     120
cgatttcgac ccgagtgctg cccccccttt caagattgca gacatccgtg ctgcaattcc     180
gccgcattgc tgggtgaaga acccctgaag gtcgctcagc tacgtcctga gagacctcct     240
tgtcatcctc agcttcgccg ttgcggcggc aaagctggac agctggactt tctggcctct     300
ttactgggtt gctcaaggaa ccatgttctg ggcagtcttt gttcttggac atgattgtgg     360
ccatgggagc ttctcagaca tctggttgtt gaacaatgtg atgggacata tactccattc     420
ctcaatcctc gtaccttacc atggatggag aattagccac aagacccatc accagaatca     480
cggcaatgtg gagaaagatg aatcctgggt tcctctaccg gagaaagtgt acaagagctt     540
```

-continued

```
ggataccagc actaagttca tgaggttcac cattcctctc ccaatgtttg cttatcctat      600
ctacttgtgg acgagaagtc cggggaagaa agggtcgcat ttcaacccat acagcgacct      660
attcgcacca aacgagaggg cagcggtctt gatttcaaca ttgtgctgga cagccatggc      720
cttactcctc tgctactcat cgttcatata cggcttcgct ccggtcctca aaatctacgg      780
cgtaccttat ctgatattcg tggcatggct cgacatggtg acctaccttc atcaccacgg      840
gtacgagcag aagctgccgt ggtacagagg caaagaatgg agctacctac gtggagggct      900
gacgaccgtt gatcgagatt acggggtcat caacaacatc accatgaca ttggcaccca      960 tgtcattcac catctcttcc ctcaaatgcc acactatcac cttgtggaag cgactcaggc     1020
agcgaagcac gtgctgggga agtactacag agagccgaag aaatcagggc ctttcccatt     1080
ccacttgttt gggtacttgg taaggagcct gggcgaggat cactacgtta gcgacacagg     1140
cgacgtcgtt ttctatcagt ctgacccaca tattcccaag ttccgtacca gcagtgccac     1200
caccaagtcc aaatccagct gatgatattt ggctctgata tatgcaggct gtttatcttg     1260
tcctttgttc gtttctttct cccagaaaca aattctctgt ttctatgttt ctctgtctct     1320 cccgcccca gctttctttc tgagtatatc gtataaagtt tcgagtgatt gtaaaagcag     1380
aaaagaagaa aagaagaaga ataataaaga ggctaagcaa ctgctctctg gttgcgttgt     1440
catggactca tggttgttaa cattgtaaca aagcagaga aattatgcac tagtagttct     1500
tctgggcaaa aaaaaaaaaa aaaaaaaaaa aaaaaa                                1536
```

<210> SEQ ID NO 2
<211> LENGTH: 53
<212> TYPE: PRT
<213> ORGANISM: Linum usitatissimum

<400> SEQUENCE: 2

```
Met Ser Pro Pro Asn Ser Met Ser Pro Thr Thr Asn Gly Asn Gly Val
  1               5                  10                  15

Ala Met Asn Gly Ala Lys Lys Gln Leu Asp Phe Asp Pro Ser Ala Ala
             20                  25                  30

Pro Pro Phe Lys Ile Ala Asp Ile Arg Ala Ala Ile Pro Pro His Cys
         35                  40                  45

Trp Val Lys Asn Pro
     50
```

<210> SEQ ID NO 3
<211> LENGTH: 1473
<212> TYPE: DNA
<213> ORGANISM: Linum usitatissimum

<400> SEQUENCE: 3

```
tattgggttt gtttggtgca gattacagtg acttcaaaac tgtggctctg cacgaccaaa       60
ctatgagccc tccaaactca atgagtcccg ccaccaacgg cagcaccaat ggtgtggcta      120
tcaatggggc gaagaagcta ctcgatttcg acccgagtgc tgctccccct ttcaagattg      180
cagacatccg tgctgcaatc ccgccgcatt gttgggtgaa gaaccctgg aggtcactca      240 gctacgtcct gagagacctc ctggtcatcc tcagcttcgc cgttgcggcg acaaagctgg      300
acagctggac tgtctggcct ctctactgga ttgctcaagg aaccatgttc tgggcagtct      360 tgttcttgg acatgattgt ggccatggga gcttctcaga cagttggttg ttgaacaacg      420
tgatgggaca tatactccat tcctcaatcc tcgtaccttac ccatggatgg agaattagcc      480
acaagaccca tcaccagaat cacggcaatg tggagaaaga tgaatcctgg gttccactgc      540
```

-continued

```
cggagaaggt gtacaagagc ttggataccg gcaccaagtt catgaggttc accatccctc    600
tcccaatgtt tgcgtatcct atctacttgt ggaggagaag tccggggaag aaagggtcgc    660
atttcaaccc atacagtgac ctgttcgcac cgaacgagag gacatcggtc atgatttcga    720
cattgtgctg gacagccatg gccttactcc tctgctactc atcgttcatc tacggcttcc    780
ttccggtctt caaaatctac ggcgtccctt atctaatatt cgtggcgtgg ctcgacatgg    840
tgacctacct tcaccaccac gggtacgagc agaagctgcc gtggtacaga ggcaaagagt    900
ggagctacct acgtggaggg ctgacgaccg tcgattgaga ttacggggtc atcaacaaca    960
tccaccatga cattggcacc catgttattc accatctctt ccctcaaatg ccacactatc   1020
acctagtcga agcgactcag gcagcgaagc acgtgctggg gaagtactac agagaaccga   1080
agaaatcagg gccttttccca ttccacttgt ttgggtactt ggtgaggagc ctgggcgagg   1140
atcactacgt tagcgataca ggcgacgtcg ttttctatca atctgaccca catattccca   1200
agttccctac cagtgccacc accaagtcca aatctagctg atgatattgg ctctgatctg   1260
atgtatgctg caggctgttt tattttgtcc tttgttcgtt tctttctgcc agaaacaaat   1320
tctctgtttc tatgtttctc tgtctctccc acccccagctt tctttctgag tatatcgtat   1380
aaagtttcaa gtgattgtaa gagcagaaaa gaaaagaaga agaagaataa taagaggat   1440
tggcaacaaa aaaaaaaaaa aaaaaaaaaa aaa                                 1473
```

<210> SEQ ID NO 4
<211> LENGTH: 291
<212> TYPE: PRT
<213> ORGANISM: Linum usitatissimum

<400> SEQUENCE: 4

```
Met Ser Pro Pro Asn Ser Met Ser Pro Ala Thr Asn Gly Ser Thr Asn
  1               5                  10                  15

Gly Val Ala Ile Asn Gly Ala Lys Lys Leu Leu Asp Phe Asp Pro Ser
             20                  25                  30

Ala Ala Pro Pro Phe Lys Ile Ala Asp Ile Arg Ala Ala Ile Pro Pro
         35                  40                  45

His Cys Trp Val Lys Asn Pro Trp Arg Ser Leu Ser Tyr Val Leu Arg
     50                  55                  60

Asp Leu Leu Val Ile Leu Ser Phe Ala Val Ala Ala Thr Lys Leu Asp
 65                  70                  75                  80

Ser Trp Thr Val Trp Pro Leu Tyr Trp Ile Ala Gln Gly Thr Met Phe
                 85                  90                  95

Trp Ala Val Phe Val Leu Gly His Asp Cys Gly His Gly Ser Phe Ser
            100                 105                 110

Asp Ser Trp Leu Leu Asn Asn Val Met Gly His Ile Leu His Ser Ser
        115                 120                 125

Ile Leu Val Pro Tyr His Gly Trp Arg Ile Ser His Lys Thr His His
    130                 135                 140

Gln Asn His Gly Asn Val Glu Lys Asp Glu Ser Trp Val Pro Leu Pro
145                 150                 155                 160

Glu Lys Val Tyr Lys Ser Leu Asp Thr Gly Thr Lys Phe Met Arg Phe
                165                 170                 175

Thr Ile Pro Leu Pro Met Phe Ala Tyr Pro Ile Tyr Leu Trp Arg Arg
            180                 185                 190

Ser Pro Gly Lys Lys Gly Ser His Phe Asn Pro Tyr Ser Asp Leu Phe
        195                 200                 205

Ala Pro Asn Glu Arg Thr Ser Val Met Ile Ser Thr Leu Cys Trp Thr
```

```
                210                 215                 220
Ala Met Ala Leu Leu Leu Cys Tyr Ser Ser Phe Ile Tyr Gly Phe Leu
225                 230                 235                 240

Pro Val Phe Lys Ile Tyr Gly Val Pro Tyr Leu Ile Phe Val Ala Trp
                245                 250                 255

Leu Asp Met Val Thr Tyr Leu His His His Gly Tyr Glu Gln Lys Leu
        260                 265                 270

Pro Trp Tyr Arg Gly Lys Glu Trp Ser Tyr Leu Arg Gly Gly Leu Thr
        275                 280                 285

Thr Val Asp
    290

<210> SEQ ID NO 5
<211> LENGTH: 1495
<212> TYPE: DNA
<213> ORGANISM: Linum usitatissimum

<400> SEQUENCE: 5
ttcaaaactg tggctctgca ggaccaaact atgagccctc caaactcaat gagtcccacc      60
accaacggca atggtgtggc tatgaatggg gcgaagaagc agctcgattt cgacccgagt     120
gctgccccccc ctttcaagat tgcagacatc cgtgctgcaa ttccgccgca ttgctgggtg    180
aagaacccct ggaggtcgct cagctacgtc ctgagagacc tccttgtcat cctcagcttc     240
gccgttgcgg cggcaaagct ggacagctgg actttctggc ctctttactg ggttgctcaa     300
ggaaccatgt tctgggcagt ctttgttctt ggacatgatt gtggccatgg agcttctca     360
gacatctggt tgttgaacaa tgtgatggga catatactcc attcctcaat cctcgtacct     420
taccatggat ggagaattag ccacaagacc atcaccagaa tcacggcaa tgtggagaaa      480
gatgaatcct gggttcctct accggagaaa gtgtacaaga gcttggatac cagcactaag    540
ttcatgaggt tcaccattcc tctcccaatg tttgcttatc ctatctactt gtggacgaga    600
agtccgggga agaaagggtc gcatttcaac ccatacagcg acctattcgc accaaacgag    660
agggcagcgg tcttgatttc aacattgtgc tggacagcca tggccttact cctctgctac    720
tcatcgttca tatacggctt cgctccggtc ctcaaaatct acggcgtacc ttatctgata    780
ttcgtggcat ggctcgacat ggtgacctac cttcatcacc acgggtacga gcagaagctg    840
ccgtggtaca gaggcaaaga atggagctac ctacgtggag ggctgacgac cgttgatcga    900
gattacgggg tcatcaacaa catccaccat gacattggca cccatgtcat tcaccatctc    960
ttccctcaaa tgccacacta tcaccttgtg gaagcgactc aggcagcgaa gcacgtgctg   1020
gggaagtact acagagagcc gaagaaatca gggccttttcc cattccactt gtttgggtac   1080
ttggtaagga gcctgggcga ggatcactac gttagcgaca caggcgacgt cgtttttctat  1140
cagtctgacc cacatattcc caagttccgt accagcagtg ccaccaccaa gtccaaatcc    1200
agctgatgat atttggctct gatatatgca ggctgtttat cttgtccttt gttcgtttct    1260
ttctcccaga aacaaattct ctgtttctat gtttctctgt ctctcccgcc cccagctttc   1320
tttctgagta tatcgtataa agtttcgagt gattgtaaaa gcagaaaaga agaaaagaag    1380
aagaataata aagaggctaa gcaactgctc tctggttgcg ttgtcatgga ctcatggttg    1440
ttaacattgt aacaaaagca gagaaattat gcactagtaa aaaaaaaaaa aaaaa         1495

<210> SEQ ID NO 6
<211> LENGTH: 391
<212> TYPE: PRT
<213> ORGANISM: Linum usitatissimum
```

<400> SEQUENCE: 6

```
Met Ser Pro Pro Asn Ser Met Ser Pro Thr Thr Asn Gly Asn Gly Val
 1               5                  10                  15
Ala Met Asn Gly Ala Lys Lys Gln Leu Asp Phe Asp Pro Ser Ala Ala
             20                  25                  30
Pro Pro Phe Lys Ile Ala Asp Ile Arg Ala Ala Ile Pro Pro His Cys
         35                  40                  45
Trp Val Lys Asn Pro Trp Arg Ser Leu Ser Tyr Val Leu Arg Asp Leu
     50                  55                  60
Leu Val Ile Leu Ser Phe Ala Val Ala Ala Lys Leu Asp Ser Trp
 65                  70                  75                  80
Thr Phe Trp Pro Leu Tyr Trp Val Ala Gln Gly Thr Met Phe Trp Ala
                 85                  90                  95
Val Phe Val Leu Gly His Asp Cys Gly His Gly Ser Phe Ser Asp Ile
            100                 105                 110
Trp Leu Leu Asn Asn Val Met Gly His Ile Leu His Ser Ser Ile Leu
        115                 120                 125
Val Pro Tyr His Gly Trp Arg Ile Ser His Lys Thr His His Gln Asn
    130                 135                 140
His Gly Asn Val Glu Lys Asp Glu Ser Trp Val Pro Leu Pro Glu Lys
145                 150                 155                 160
Val Tyr Lys Ser Leu Asp Thr Ser Thr Lys Phe Met Arg Phe Thr Ile
                165                 170                 175
Pro Leu Pro Met Phe Ala Tyr Pro Ile Tyr Leu Trp Thr Arg Ser Pro
            180                 185                 190
Gly Lys Lys Gly Ser His Phe Asn Pro Tyr Ser Asp Leu Phe Ala Pro
        195                 200                 205
Asn Glu Arg Ala Ala Val Leu Ile Ser Thr Leu Cys Trp Thr Ala Met
    210                 215                 220
Ala Leu Leu Leu Cys Tyr Ser Ser Phe Ile Tyr Gly Phe Ala Pro Val
225                 230                 235                 240
Leu Lys Ile Tyr Gly Val Pro Tyr Leu Ile Phe Val Ala Trp Leu Asp
                245                 250                 255
Met Val Thr Tyr Leu His His Gly Tyr Glu Gln Lys Leu Pro Trp
            260                 265                 270
Tyr Arg Gly Lys Glu Trp Ser Tyr Leu Arg Gly Gly Leu Thr Thr Val
        275                 280                 285
Asp Arg Asp Tyr Gly Val Ile Asn Asn Ile His His Asp Ile Gly Thr
    290                 295                 300
His Val Ile His His Leu Phe Pro Gln Met Pro His Tyr His Leu Val
305                 310                 315                 320
Glu Ala Thr Gln Ala Ala Lys His Val Leu Gly Lys Tyr Tyr Arg Glu
                325                 330                 335
Pro Lys Lys Ser Gly Pro Phe Pro Phe His Leu Phe Gly Tyr Leu Val
            340                 345                 350
Arg Ser Leu Gly Glu Asp His Tyr Val Ser Asp Thr Gly Asp Val Val
        355                 360                 365
Phe Tyr Gln Ser Asp Pro His Ile Pro Lys Phe Arg Thr Ser Ser Ala
    370                 375                 380
Thr Thr Lys Ser Lys Ser Ser
385                 390
```

<210> SEQ ID NO 7

-continued

```
<211> LENGTH: 1130
<212> TYPE: DNA
<213> ORGANISM: Linum usitatissimum

<400> SEQUENCE: 7
catggccaag cttattccca caaaagggtc gaaacaaaag gaaaatggtc tgattgtctg      60
ctaaagttta ttcagtacgt gggtggatgt tttgttcacc tttacagtgg catctttacc    120
acagctgtta ccagcatcac tcgtcatcat cattaatcct tagttacgat acattctttc    180
tccaaattac taacatcttt cctgatttat accataagat aatccatcta ttattcgatt    240
gcaaagtaat agaatggtaa gagtttcgac taagttcaaa taaatccaaa gtttgaatct    300
tgacatcaag gtaaaataat acataggtgt gtgaaaaatg gtaagactca tccatgtctc    360
tgccctcctc ccaacccatt acatgacgtc agaaagagct cgtacttcac attctcggac    420
cgaaggacaa ccatgctttg ttgacatctc cgaaaggcaa ccaattatac ccctagtga    480 tcctaaacac atgcacatgt ccctatgccc gaacttgctc cctaaatatt gcagcatcaa    540
cattgcaatt cagagtcccc caaacaagac cgatgcccac ttgagccaca ttagttgatt    600
agtcgatttc gccctagctc ccgctaaccg atcgtagcca ctccaccaag tcactaatcc    660
ttgattaaag agttaaacaa gttgatatca cacctgtggt aactcatgca cataccattg    720
aagaaagttg ccatgtgtta gaatcaagga tttgcccacc accattgata ctgaaattga    780
agaatgctag ctagcaggca gcaacggctc cttttcattt gtctttcaac agagcaagta    840
acaacaaccg ttgcctaaac tgaaacccaa taaagagcag aaaaaagggt tgggtggtgt    900
aggctagttt gtctgaaatc aatgtacatt ttgcacttcc atttactctt ctccatccac    960
ttggcatcct acattattac ttcttcttcg ttagctctca ccaaacttta catacacttt   1020
ttcggttata aatactgtga gcctcaaagc aaaggccact cactctattc attattatta   1080
aaaaaaaaat attggttgtt tggtgcagat tatagtgact tcaaaactgt                1130

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaatgtttg cgtatcctat c                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccaagtac ccaaacaagt g                                                21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
```
attcgcacca aacgagaggg cag                                             23

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacaatgttg aaatcaagac cgctgc                                          26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatcctaat acgactcact atagggc                                         27

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caacggcagc accaatg                                                    17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgacccttt cttcccc                                                    17

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgggatatca ctcagcataa tg                                              22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aattaaccct cactaaaggg                                                 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcaaaactg tggctctgca g                                         21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctcagaaaga aagctgggggg c                                        21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcacattgtt caacaaccag a                                         21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccttatcta atattcgtgg cg                                        22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttggtggtg gcactggtag                                           20

<210> SEQ ID NO 22
<211> LENGTH: 1061
<212> TYPE: DNA
<213> ORGANISM: Linum usitatissimum

<400> SEQUENCE: 22
cccttatcta atattcgtgg cgtggctcga catggtgacc taccttcacc accacgggta      60
cgagcagaag ctgccgtggt acagaggcaa agagtggagc tacctacgtg gagggctgac     120
gaccgtcgat tgagattacg gggtcatcaa caacatccac catgacattg gcacccatgt     180

-continued

```
tattcaccat ctcttccctc aaatgccaca ctatcaccta gtcgaagcgg taaggaggtc      240
ttgattatta acttaatgtt tttgttgtta taatttgagt ccgattctgg agtcagggga      300
tttccttctt ggatccgatc caggatcaag ctggtccctt gaatttctat atgatcttat      360
attaattaag gataatgtgg tcatatgttt ttaaatattt ttgtttacca tcattttcga      420
tcaccggaaa atgtcctgag cagttttccg gtcactttaa cctccattga caaatttttt      480
cacccacatg atcaccctag ccgggtttac gtttattgaa aatttttatt tttttgaatt      540
ttttttcgat gaccaactgt acaactttgt attgaaagtt gtatggatca tacaaatgtg      600
tatgtacaaa agtatattct aagtactata ctaagcatta cttagtatta cgtttctaca      660
aacctataga gaaatgcata caattttgta tagaacttag tatacacgta gctgtgaaat      720
gtcaatttcc ctccgtattt tcagagacaa gacatgattt ttagactggc agattttttt      780
tatcggatag atttctccaa cttcagattc ggactggatt attaactata ttattcatca      840
actctgacgt tgatgttgc atgtgacaga ctcaggcagc gaagcacgtg ctggggaagt       900
actacagaga accgaagaaa tcagggcctt tcccattcca cttgtttggg tacttggtga      960
ggagcctggg cgaggatcac tacgttagcg atacaggcga cgtcgttttc tatcaatctg     1020
acccacatat tcccaagttc cctaccagtg ccaccaccaa g                          1061
```

<210> SEQ ID NO 23
<211> LENGTH: 469
<212> TYPE: DNA
<213> ORGANISM: Linum usitatissimum

<400> SEQUENCE: 23

```
ttcaaaactg tggctctgca ggaccaaact atgagccctc caaactcaat gagtcccacc       60
accaacggca atggtgtggc tatgaatggg gcgaagaagc agctcgattt cgacccgagt      120 gctgccccccc ctttcaagat tgcagacatc cgtgctgcaa ttccgccgca ttgctgggtg     180
aagaacccct gaaggtcgct cagctacgtc ctgagagacc tccttgtcat cctcagcttc      240
gccgttgcgg cggcaaagct ggacagctgg actttctggc ctctttactg ggttgctcaa      300
ggaaccatgt tctgggcagt cttgttcttt ggacatgatt ggtaaactaa tttcacattt      360
tctttctggt aatgtgggtt ttattgaaaa agattaaaac ttttatctg ggttgttgca      420 tgcagtggcc atgggagctt ctcagacatc tggttgttga acaatgtga                  469
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ggtttgtttg gtgcagatta c                                                 21
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
tcagagccaa tatcatcagc ta                                                22
```

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 26
tagacataat gagccctcca aactcaa                                        27

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 27
agagccaaat atcatcagct g                                              21

<210> SEQ ID NO 28
<211> LENGTH: 1200
<212> TYPE: DNA
<213> ORGANISM: Linum usitatissimum

<400> SEQUENCE: 28
tagacataat gagccctcca aactcaatga gtcccgccac caacggcagc accaatggtg      60
tggctatcaa tggggcgaag aagctactcg atttcgaccc gagtgctgct cccccttca     120 agattgcaga catccgtgct gcaatcccgc gcattgttg ggtgaagaac ccctggaggt     180
cactcagcta cgtcctgaga gacctcctgg tcatcctcag cttcgccgtt gcggcgacaa     240
agctggacag ctggactgtc tggcctctct actggattgc tcaaggaacc atgttctggg     300
cagtctttgt tcttggacat gattgtggcc atggagcttt ctcagacagt tggttgttga     360
acaacgtgat gggacatata ctccattcct caatcctcgt accttaccat ggatggagaa     420
ttagccacaa gacccatcac cagaatacg gcaatgtgga gaaagatgaa tcctgggttc     480
cactgccgga gaaggtgtac aagagcttgg ataccggcac caagttcatg aggttcacca     540
tccctctccc aatgtttgcg tatcctatct acttgtggag gagaagtccg gggaagaaag     600
ggtcgcattt caacccatac agtgacctgt tcgcaccgaa cgagaggaca tcggtcatga     660
tttcgacatt gtgctggaca gccatggcct tactcctctg ctactcatcg ttcatctacg     720
gcttccttcc ggtcttcaaa atctacggcg tcccttatct aatattcgtg gcgtggctcg     780
acatggtgac ctaccttcac caccacgggt acgagcagaa gctgccgtgg tacagaggca     840
aagagtggag ctacctacgt ggagggctga cgaccgtcga tcgagattac ggggtcatca     900
acaacatcca ccatgacatt ggcacccatg ttattcacca tctcttccct caaatgccac     960
actatcacct agtcgaagcg actcaggcag cgaagcacgt gctggggaag tactacagag    1020
aaccgaagaa atcagggcct ttcccattcc acttgtttgg gtacttggtg aggagcctgg    1080
gcgaggatca ctacgttagc gatacaggcg acgtcgtttt ctatcaatct gacccacata    1140
ttcccaagtt ccctaccagt gccaccacca agtccaaatc tagctgatga tattggctca    1200

<210> SEQ ID NO 29
<211> LENGTH: 1198
<212> TYPE: DNA
<213> ORGANISM: Linum usitatissimum

<400> SEQUENCE: 29

```
agacataatg agccctccaa actcaatgag tcccaccacc aacggcaatg gtgtggctat      60
gaatggggcg aagaagcagc tcgatttcga cccgagtgct gcccccccett tcaagattgc    120
agacatccgt gctgcaattc cgccgcattg ctgggtgaag aaccectgga ggtcgctcag    180
ctacgtcctg agagacctcc ttgtcatcct cagcttcgcc gttgcggcgg caaagctgga    240
cagctggact ttctggcctc tttactgggt tgctcaagga accatgttct gggcagtctt    300
tgttcttgga catgattgtg gccatgggag cttctcagac atctggttgt gaacaatgt     360
gatgggacat atactccatt cctcaatcct cgtaccttac catggatgga gaattagcca    420
caagacccat caccagaatc acggcaatgt ggagaaagat gaatcctggg ttcctctacc    480
ggagaaagtg tacaagagct ggataccag cactaagttc atgaggttca ccattcctct     540
cccaatgttt gcttatccta tctacttgtg gacgagaagt ccggggaaga aagggtcgca    600
tttcaaccca tacagcgacc tattcgcacc aaacgagagg gcagcggtct tgatttcaac    660
attgtgctgg acagccatgg ccttactcct ctgctactca tcgttcatat acggcttcgc    720
tccggtcctc aaaatctacg gcgtacctta tctgatattc gtggcatggc tcgacatggt    780
gacctacctt catcaccacg ggtacgagca aagctgccg tggtacagag gcaaagaatg     840
gagctaccta cgtggagggc tgacgaccgt tgatcgagat tacggggtca tcaacaacat    900
ccaccatgac attggcaccc atgtcattca ccatctcttc cctcaaatgc cacactatca    960
ccttgtggaa gcgactcagg cagcgaagca cgtgctgggg aagtactaca gagagccgaa   1020
gaaatcaggg ccctttccat tccacttgtt tgggtacttg gtaaggagcc tgggcgagga   1080
tcactacgtt agcgacacag gcgacgtcgt tttctatcag tctgacccac atattcccaa   1140
gttccgtacc agcagtgcca ccaccaagtc caaatccagc tgatgatatt tggctcta    1198
```

<210> SEQ ID NO 30
<211> LENGTH: 1199
<212> TYPE: DNA
<213> ORGANISM: Linum usitatissimum

<400> SEQUENCE: 30

```
gacataatga gccctccaaa ctcaatgagt cccgccacca acggcagcac caatggtgtg      60
gctatcaatg gggcgaagaa gctactcgat ttcacccga gtgctgctcc ccctttcaag     120
attgcagaca tccgtgctgc aatcccgccg cattgttggg tgaagaaccc ctggaggtca    180
ctcagctacg tcctgagaga cctcctggtc atcctcagct tcgccgttgc ggcgacaaag    240
ctggacagct ggactgtctg gcctctctac tggattgctc aaggaaccat gttctgggca    300
gtctttgttc ttggacatga ttgtggccat gggagcttct cagacagttg gttgttgaac    360
aacgtgatgg gacatatact ccattcctca atcctcgtac cttaccatgg atggagaatt    420
agccacaaga cccatcacca gaatcacggc aatgtggaga agatgaatc ctgggttcca    480
ctgccggaga aggtgtacaa gagcttggat accggcacca agttcatgag gttcaccatc    540
cctctcccaa tgtttgcgta tcctatctac ttgtggagga agtccgggg aagaaagggg    600
tcgcatttca acccatacag tgacctgttc gcaccgaacg agaggacatc ggtcatgatt    660
tcgacattgt gctggacagc catggcctta ctcctctgct actcatcgtt catctacggc    720
ttccttccgg tcttcaaaat ctacggcgtc cctatctaa tattcgtggc gtggctcgac    780
atggtgacct accttcacca ccacgggtac gagcagaagc tgccgtggta cagaggcaaa    840
gagtggagct acctacgtgg agggctgacg accgtcgatt gagattacgg ggtcatcaac    900
```

```
aacatccacc atgacattgg cacccatgtt attcaccatc tcttccctca aatgccacac      960
tatcacctag tcgaagcgac tcaggcagcg aagcacgtgc tggggaagta ctacagagaa     1020
ccgaagaaat cagggccttt cccattccac ttgtttgggt acttggtgag gagcctgggc     1080
gaggatcact acgttagcga tacaggcgac gtcgttttct atcaatctga cccacatatt     1140
cccaagttcc ctaccagtgc caccaccaag tccaaatcta gctgatgata ttggctcta      1199
```

<210> SEQ ID NO 31
<211> LENGTH: 1198
<212> TYPE: DNA
<213> ORGANISM: Linum usitatissimum

<400> SEQUENCE: 31

```
agacataatg agccctccaa actcaatgag tcccaccacc aacggcaatg gtgtggctat       60
gaatggggcg aagaagcagc tcgatttcga cccgagtgct gccccccctt tcaagattgc      120
agacatccgt gctgcaattc cgccgcattg ctgggtgaag aacccctgaa ggtcgctcag      180
ctacgtcctg agagacctcc ttgtcatcct cagcttcgcc gttgcggcgg caaagctgga      240
cagctggact ttctggcctc tttactgggt tgctcaagga accatgttct gggcagtctt      300
tgttcttgga catgattgtg gccatgggag cttctcagac atctggttgt tgaacaatgt      360
gatgggacat atactccatt cctcaatcct cgtaccttac catggatgga gaattagcca      420
caagacccat caccagaatc acggcaatgt ggagaaagat gaatcctggg ttcctctacc      480
ggagaaagtg tacaagagct tggataccag cactaagttc atgaggttca ccattcctct      540
cccaatgttt gcttatccta tctacttgtg gacgagaagt ccggggaaga aagggtcgca      600
tttcaaccca tacagcgacc tattcgcacc aaacgagagg gcagcggtct tgatttcaac      660
attgtgctgg acagccatgg ccttactcct ctgctactca tcgttcatat acggcttcgc      720
tccggtcctc aaaatctacg gcgtaccttaa tctgatattc gtggcatggc tcgacatggt     780
gacctacctt catcaccacg ggtacgagca gaagctgccg tggtacagag gcaaagaatg      840
gagctaccta cgtggagggc tgacgaccgt tgatcgagat tacggggtca tcaacaacat      900
ccaccatgac attggcaccc atgtcattca ccatctcttc cctcaaatgc cacactatca      960
ccttgtggaa gcgactcagg cagcgaagca cgtgctgggg aagtactaca gagagccgaa     1020
gaaatcaggg cctttcccat tccacttgtt tgggtacttg gtaaggagcc tgggcgagga     1080
tcactacgtt agcgacacag gcgacgtcgt tttctatcag tctgacccac atattcccaa     1140
gttccgtacc agcagtgcca ccaccaagtc caaatccagc tgatgatatt tggctcta       1198
```

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 32

```
cagtgacctg ttcgcaccg                                                     19
```

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 33
cccggctagg gtgatcatg                                                  19

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
actacctgca aaccaaaaca gatt                                            24

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catagtttgg tcgtgcagac gg                                              22

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gattgtctgc taaagtttat tcag                                            24

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
catagccaca ccattgccg                                                  19

<210> SEQ ID NO 38
<211> LENGTH: 1151
<212> TYPE: DNA
<213> ORGANISM: Linum usitatissimum

<400> SEQUENCE: 38
attgtctgct aaagtttatt cagtacgtgg gtggatgttt tgttcacctt tacagtggca     60
tctttaccac agctgttacc agcatcactc gtcatcatca ttaatcctta gttacgatac    120
attctttctc caaattacta acatctttcc tgatttatac cataagataa tccatctatt    180
attcgattgc aaagtaatag aatggtaaga gtttcgacta agttcaaata aatccaaagt    240
ttgaatcttg acatcaaggt aaaataatac ataggtgtgt gaaaaatggt aagactcatc    300
catgtctctg ccctcctccc aacccattac atgacgtcag aaagagctcg tacttcacat    360
tctcggaccg aaggacaacc atgctttgtt gacatctccg aaaggcaacc aattataccc    420
cctagtgatc ctaaacacat gcacatgtcc ctatgcccga acttgctccc taaatattgc    480
```

-continued

```
agcatcaaca ttgcaattca gagtccccca aacaagaccg atgcccactt gagccacatt      540
agttgattag tcgatttcgc cctagctccc gctaaccgat cgtagccact ccaccaagtc      600
actaatcctt gattaaagag ttaaacaagt tgatatcaca cctgtggtaa ctcatgcaca      660
taccattgaa gaaagttgcc atgtgttaga atcaaggatt tgcccaccac cattgatact      720
gaaattgaag aatgctagct agcaggcagc aacggctcct tttcatttgt ctttcaacag      780
agcaagtaac aacaaccgtt gcctaaactg aaacccaata aagagcagaa aaaagggttg      840
ggtggtgtag gctagtttgt ctgaaatcaa tgtacatttt gcacttccat ttactcttct      900
ccatccactt ggcatcctac attattactt cttcttcgtt agctctcacc aaactttaca      960
tacacttttt cggttataaa tactgtgagc ctcaaagcaa aggccactca ctctattcat     1020
tattattaaa aaaaaaatat tggttgtttg gtgcagatta tagtgacttc aaaactgtgg     1080
ctctgcagga ccaaactatg agccctccaa actcaatgag tcccaccacc aacggcaatg     1140
gtgtggctat g                                                          1151

<210> SEQ ID NO 39
<211> LENGTH: 1107
<212> TYPE: DNA
<213> ORGANISM: Linum usitatissimum

<400> SEQUENCE: 39
actacctgca aaccaaaaca gattcatggc caagcttatt cccacaaaag ggtccaaaca       60
aaaggaaaat ggtctgattg tctgctaaag tttattgatc agtacgtggg tggatgtttt      120
gttcaccttt acagtgccat tctttaccac agttgttacc agcatcactc atcatcatca      180
gcatcattaa tccttagttt tctatgcact cactttcatt agtgttcact ttgcaattca      240
ataatccatc tattattcga ttgcaaagca agagagttgt aagagtttcg actaagttca      300
aatggagccc aaagtttgat catcagtttg tgaaaacaaa gtcaagctcg tccatatctc      360
tgccttgttc ccaacccact acatagcatc tggaagacct cgtacttcac attctcggac      420
cgaaggacaa ccaatacccc ccttgtgatc ctaaacacat gcacaaatcc ctctgcccga      480
aacttgcccg aacttactcc ctaagaccga tgcccacttg agtcacatga gttgattagt      540
cgattccacc ctagctcccg cgaactcagc agtgcccgtt gcgactccgc caaatcacta      600
atccttaatt aaaagaacta ataagttgat atcatcacat ttgtggtaac tcatgcatgc      660
acataggttt cctagatacc attgaaggaa gttgccatgt gtttgaatca agatttgcc      720 caccaccatt gatactgaaa ttgaagaacc tagcagccag caacggctcc ttttcatttg      780
tctttcaaca gagcaagtaa caacaaccgt tgcctaaact gaaacccaat aaagagcaaa      840
aaaaaagggg ttgggtggtg taggctagtt tgtctgaaat cagtgtacat tttgcatttc      900
catttactct tctccatcca cttggcatcc tgcattactt cttcttcgtt agttctcacc      960
aacctacata ctcttcggtt ataaatactg tgaggctgaa accaaggcc actcagtcta     1020 ttcattatta ttcaaaaata tatattgggt ttgtttggtg cagattacag tgacttcaaa     1080
actgtggctc tgcacgacca aactatg                                         1107
```

US 8,088,978 B2

OMEGA-3 FATTY ACID DESATURASE FAMILY MEMBERS AND USES THEREOF

RELATED APPLICATIONS

This application is a 35 U.S.C. 371 national stage filing of International Application No. PCT/CA2006/000156, filed Feb. 7, 2006, which claims priority to U.S. Provisional Application No. 60/651,568, filed Feb. 9, 2005, the entire contents of which are hereby incorporated by reference herein.

BACKGROUND OF THE INVENTION

There are two types of linseed flax produced; one is an industrial oil type containing more than 50% linolenic acid. The second type is an edible oil crop containing less than 2% linolenic acid. Solin is an example of a low linolenic type, while the variety Normandy has high levels of linolenic acid.

Mutant strains of flax containing low levels of linolenic acid have been developed using ethyl methanesulphonate (EMS) mutagenesis of high linolenic acid cultivars (Green and Marshall (1984) Euphytica 33:321-328; Rowland (1991) Can. J. Plant Sci. 71:393-39). Mutations in omega-3 desaturase genes, i.e., the genes encoding the enzymes controlling omega-3 fatty acid desaturation, are known to reduce linolenic acid levels in other plants (Browse et al. (1993) J Biol Chem. 268(22):16345-51).

In flax, two genes control the low linolenic acid trait (Green and Marshall (1984); Rowland (1991)) suggesting that flax may contain two omega-3 fatty acid desaturase (FAD3) genes. However, only one FAD3 gene from flax has been isolated (Qiu et al. (2003), WO 02102970) and the mutations resulting in the low linolenic acid trait have not been characterized at the molecular level.

Accordingly, the identification of markers for the linolenic acid trait in flax would be helpful to plant breeders.

SUMMARY OF THE INVENTION

The present invention relates to the isolation of a second omega-3 fatty acid desaturase (FAD3) gene in flax (*Linum usitatissimum*) and its promoter region, as well as the identification of FAD3 mutant alleles. The FAD3 genes encode the enzymes which control omega-3 fatty acid desaturation and, thus, the levels of linolenic acid (18:3(n-3)). Accordingly, the molecules of the present invention can be utilized, for example, to develop markers for the mutations in flax FAD3 genes. Specifically, such markers can be used to accelerate the breeding process, particularly for seed traits, since selection can occur prior to seed development. Markers are also useful for germplasm identification and characterization. Further, the isolation of flax FAD3 genes and promoters of the present invention can be used to control the level and pattern of FAD3 expression and, thus, the level of 18:3 in plants. In plant transformation, seed-specific promoters are also desirable for the efficient modification of seed composition. For transformation projects, the availability of a large number of promoters can be important, as a single promoter may show variable effectiveness with a number of genes.

The invention is described for the purpose of demonstration with methods and sequences related to FAD3 genes and the promoter of one FAD3 gene. It is recognized, however, that within the scope of the invention, the utility of the invention will include employing the illustrative method to identify and use the genes from other plants which have a sufficient degree of nucleotide and amino acid identity, and genes with proper changes made by a person skilled in the art.

The present invention is based, at least in part, on the discovery of novel members of the family of omega-3 desaturase (FAD3) genes in flax (*Linum usitatissimum*). In particular, the present invention has identified a second FAD3 gene (designated herein as "FAD3B"), a corresponding promoter, and mutant allele. The present invention has also identified a mutant allele of the previously discovered FAD3 gene ("FAD3A"). These FAD3 genes are involved in the biosynthesis of long chain polyunsaturated fatty acids, for example, by encoding a form of the flax delta-15 desaturase (Δ15) which catalyzes or, in the case of a mutant allele, fails to catalyze the formation of the double bond at position fifteen (15) in linoleic acid. Formation of the double bond converts linoleic acid to linolenic acid.

In one embodiment, the invention features an isolated nucleic acid molecules that include the nucleotide sequence set forth in SEQ ID NO:1, SEQ ID NO:3, or SEQ ID NO:5. In another embodiment, the invention features isolated nucleic acid molecules that encode polypeptides having the amino acid sequence set forth in SEQ ID NO:2, SEQ ID NO:4, or SEQ ID NO:6.

In still other embodiments, the invention features isolated nucleic acid molecules having nucleotide sequences that are substantially identical (e.g., 95% identical) to the nucleotide sequence set forth as SEQ ID NO:1, SEQ ID NO:3, or SEQ ID NO:5.

The invention further features an isolated nucleic acid molecule which is capable of directing gene expression in developing plant seeds (e.g., an oilseed crop) and includes the nucleotide sequence set forth in SEQ ID NO:7, or a functional portion thereof, or a nucleic acid sequence that is at least about 76% identical to the nucleotide sequence of SEQ ID NO:7. In another embodiment nucleic acid molecule which is capable of directing gene expression in developing plant seeds is operatively linked to a gene (e.g., a gene related to fatty acid biosynthesis or lipid biosynthesis, such as a desaturase).

In a related aspect, the invention provides vectors including the isolated nucleic acid molecules which include the nucleotide sequences set forth in SEQ ID NO:5 or SEQ ID NO:7 (e.g., a desaturase-encoding nucleic acid molecule or its promoter region). Also featured are host cells including such vectors (e.g., host cells including vectors suitable for producing desaturase nucleic acid molecules and polypeptides) and methods for producing the polypeptides encoded by SEQ ID NO:5 or methods which utilize the seed-specific promoter having the nucleotide sequence of SEQ ID NO:7.

In another aspect, the invention features isolated polypeptides which include the amino acid sequences set forth as SEQ ID NO:2, SEQ ID NO:4, or SEQ ID NO:6, as well as polypeptides which are encoded by the nucleotide sequences set forth in SEQ ID NO:1, SEQ ID NO:3, or SEQ ID NO:5.

In still other embodiments, the invention features isolated polypeptides including amino acid sequences that are substantially identical (e.g., 95% identical) to the amino acid sequence set forth as SEQ ID NO:2, SEQ ID NO:4, or SEQ ID NO:6.

In another embodiment of the invention, methods of transforming a plant cell are provided. The methods include the steps of introducing into a cell a nucleic acid molecule having the nucleotide sequence set forth in SEQ ID NO:5, a nucleotide sequence which is at least about 95% identical to the nucleotide sequence set forth in SEQ ID NO:5, or a nucleotide sequence which encodes a polypeptide having the amino acid sequence set forth in SEQ ID NO:6. Transgenic plants produced by such methods are also encompassed by the present invention, e.g., an oilseed plant such as flax (*Li-* num sp.), rapeseed (*Brassica* sp.), soybean (Glycine and *Soja* sp.), sunflower (*Helianthus* sp.), corron (*Gossypium* sp.), corn (*Zea mays*), olive (*Olea* sp.), safflower (*Carthamus* sp.), cocoa (*Theobroma cacoa*), and peanut (*Arachis* sp.).

In a related aspect, the present invention features transgenic seeds having a transgene integrated into the genome of the seed, wherein the transgene includes an isolated nucleic acid molecule having the nucleotide sequence set forth in SEQ ID NO:5, a nucleotide sequence which is at least about 95% identical to the nucleotide sequence set forth in SEQ ID NO:5, or a nucleotide sequence which encodes the polypeptide having the amino acid sequence set forth in SEQ ID NO:6. Such plant seeds include, for example, an oilseed plant seed such as flax (*Linum* sp.) seeds, rapeseed (*Brassica* sp.) seeds, soybean (Glycine and *Soja* sp.) seeds, sunflower (*Helianthus* sp.) seeds, corron (*Gossypium* sp.) seeds, corn (*Zea mays*) seeds, olive (*Olea* sp.) seeds, safflower (*Carthamus* sp.) seeds, cocoa (*Theobroma cacoa*), seeds and peanut (*Arachis* sp.) seeds.

In another embodiment, the invention features methods of increasing the formation of linolenic acid in a plant cell, methods of modulating the production of linolenic acid in a plant cell, and methods for modulating the production of linolenic acid in a plant cell, e.g., a plant cell capable of generating linoleic acid such as an oilseed plant cell. Such methods include the step of transforming the cell with the nucleic acid molecule having the nucleotide sequence set forth in SEQ ID NO:5, a nucleotide sequence which is at least about 95% identical to the nucleotide sequence set forth in SEQ ID NO:5, or a nucleotide sequence which encodes the polypeptide having the amino acid sequence set forth in SEQ ID NO:6.

Methods for transforming a plant cell (e.g., an oilseed plant cell) with a nucleic acid molecule, for example, a nucleic acid molecule capable of directing seed-specific expression in a plant, having the nucleotide sequence set forth in SEQ ID NO:7, a functional portion thereof, or a nucleic acid sequence that is at least about 76% identical to the nucleotide sequence of SEQ ID NO:7 are also provided. The nucleic acid molecule can further include a gene, e.g., a gene related to fatty acid biosynthesis or lipid biosynthesis such as a desaturase gene operatively linked to the nucleotide sequence set forth in SEQ ID NO:7, a functional portion thereof, or a nucleic acid sequence that is at least about 76% identical to the nucleotide sequence of SEQ ID NO:7. Transgenic seeds and transgenic plants produced by such methods are also encompassed by the present invention.

In another embodiment, the invention features methods for identifying the genotype of a flax plant at the FAD3A and FAD3B loci. Such methods include the steps of isolating genomic DNA from the flax plant, amplifying the genomic DNA with primers designed based on SEQ ID NOs:1, 3, 5, and/or 7, and identifying the genotype of the flax plant based on these fragments. The methods can further include the step of digesting the amplified molecules with a restriction enzyme. The methods can further include the step of selecting flax plants having mutated FAD3 genes. In one embodiment, the primers used for amplifying the genomic DNA have the nucleotide sequences set forth in SEQ ID NOs:32 and 33 or SEQ ID NOs:17 and 19. In still another embodiment, the enzyme used to digest the DNA is PvuI or BsaJI.

In yet another embodiment, the invention features methods for identifying a mutation in a flax FAD3 gene. Such methods include the steps of obtaining a flax FAD3 gene using primers designed based on SEQ ID NOs:1, 3, 5, and/or 7, and assaying nucleotide sequence of the gene to determine where mutations occur. The methods can further include the step of selecting mutated genes.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE FIGURES

FIG. 2 is a table showing that 18:2(9,12) (linoleic acid) was desaturated to 18:3(9,12,15)(linolenic acid) in cultures containing LuFAD3A or LuFAD3B from Normandy. However, cultures containing either LuFAD3A or LuFAD3B from Solin showed no evidence of desaturation of linoleic acid.

DETAILED DESCRIPTION OF THE INVENTION

Figure 1:
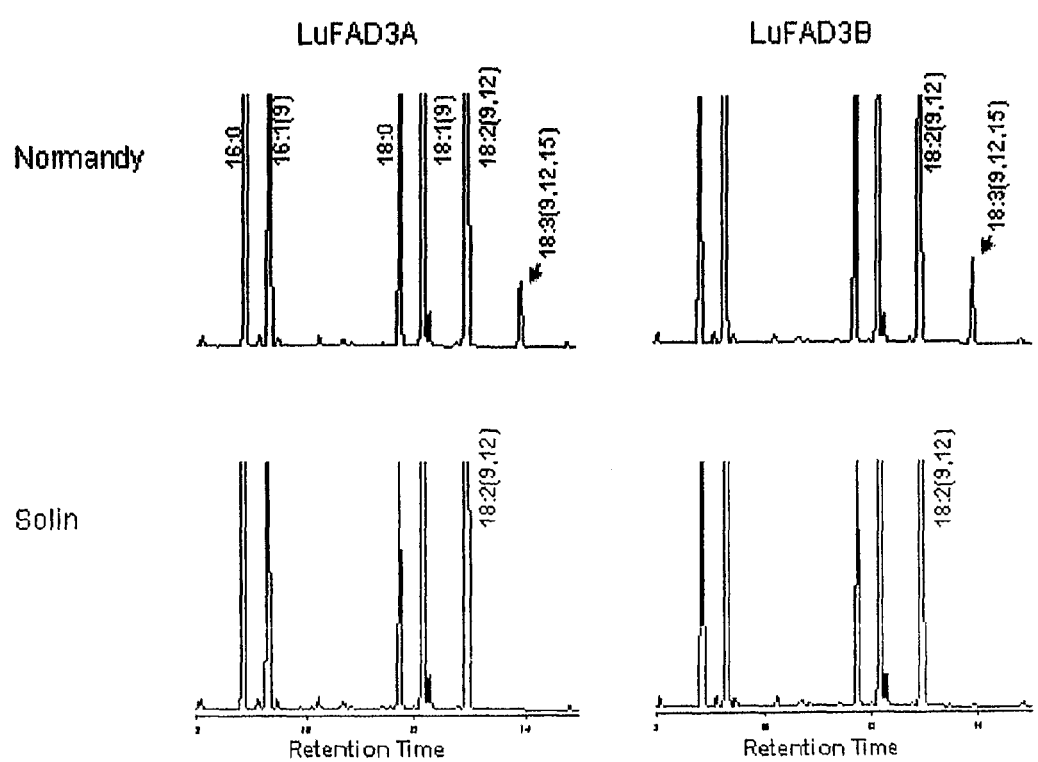
FIG. 1 shows gas chromatographic analyses of yeast cells transformed with expression vectors containing the coding regions of LuFAD3A Normandy, LuFAD3B Normandy, LuFAD3A Solin, and LuFAD3B Solin. Cultures were fed with linoleic acid.

The present invention is based, at least in part, on the discovery of novel members of the family of omega-3 desaturase (FAD3) genes in flax (*Linum usitatissimum*). In particular, the present invention has identified a second FAD3 gene (designated herein as "FAD3B"), a corresponding promoter and mutant allele. The present invention has also identified a mutant allele of the previously discovered FAD3 gene ("FAD3A"). These FAD3 genes are involved in the biosynthesis of long chain polyunsaturated fatty acids, for example, by encoding a form of the flax delta-15 desaturase ($\Delta 15$) which catalyzes or, in the case of a mutant allele, fails to catalyze the formation of the double bond at position fifteen (15) in linoleic acid. Formation of the double bond converts linoleic acid to linolenic acid.

These molecules can be utilized, for example, to develop markers for the identification of mutations in flax FAD3 genes. Such markers can be used to accelerate the breeding process, particularly for seed traits, since selection can occur prior to seed development. Markers are also useful for germplasm identification and characterization. In addition, the described wildtype FAD3B gene can be used to modulate (e.g., increase) the linolenic acid content of plants. The described FAD3 promoter can be utilized to improve seed traits, modify the fatty acid composition of seed oil and amino acid composition of seed storage protein, and produce bioactive compounds in plant seeds. Accordingly, the present invention features the above-mentioned isolated molecules, as well as methods of using these molecules as markers or to transform plants such that the proteins of the invention are expressed.

In order that the present invention may be more readily understood, certain terms are first defined. Additional definitions are set forth throughout the detailed description.

As used herein, the term "fatty acids" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18) and which may be saturated or unsaturated. "Unsaturated" fatty acids contain cis double bonds between the carbon atoms. "Polyunsaturated" fatty acids contain more than one double bond and the double bonds are arranged in a methylene interrupted system (—CH=CH—CH$_2$—CH=CH—). Fatty acids encompassed by the present invention include, for example, linoleic acid and linolenic acid.

Fatty acids are described herein by a numbering system in which the number before the colon indicates the number of carbon atoms in the fatty acid, whereas the number after the colon is the number of double bonds that are present. In the case of unsaturated fatty acids, this is followed by a number in parentheses that indicates the position of the double bonds. Each number in parenthesis is the lower numbered carbon atom of the two connected by the double bond. For example, oleic acid can be described as 18:1(9) and linoleic acid be described as 18:2(9, 12) indicating 18 carbons, one double bond at carbon 9 and 18 carbons, two double bonds at carbons 9 and 12, respectively.

As used herein, the terms "linoleic acid" and "linolenic acid" are art recognized, both of which include an 18 carbon polyunsaturated fatty acid molecule with linoleic acid containing 2 double bonds (18:2(9,12)) and linolenic containing 3 double bonds (18:3(9,12,15)).

As used herein, the terms "desaturase" or "fatty acid desaturase (FAD)" are used interchangeably and are art recognized. In the present invention, for example, the omega-3 desaturase (formerly Δ15 desaturase) from *Linum usitatissimum* (FAD3B or LuFD3B) is a desaturase that can introduce a double bond at position 15 of linoleic acid.

The term "family" when referring to the protein and nucleic acid molecules of the present invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

Isolated nucleotides of the present invention have a nucleotide sequence sufficiently identical to SEQ ID NO:1, SEQ ID NO:3, SEQ ID NO:5, and SEQ ID NO:7, respectively. Isolated polypeptides of the present invention have an amino acid sequence sufficiently identical to the amino acid sequence of SEQ ID NO:2, SEQ ID NO:4, or SEQ ID NO:6, respectively. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 85%, 90%, 95%, 96%, 97%, 98%, 99% or more homology or identity and share a common functional activity are defined herein as sufficiently identical.

In one embodiment, an isolated nucleic acid molecule has a nucleotide sequence at least about 50%, 55%, 60%, 65%, 70%, 75%, 80%, 85%, 85%, 90%, 95%, 96%, 97%, 98%, 99% or more homologous or identical to the nucleotide sequence of SEQ ID NO:1, SEQ ID NO:3, SEQ ID NO:5, or SEQ ID NO:7 or encodes an isolated polypeptide which has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:2, SEQ ID NO:4, or SEQ ID NO:6.

In another embodiment, an isolated polypeptide has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:2, SEQ ID NO:4, or SEQ ID NO:6 or is encoded by an isolated nucleic acid molecule which has a nucleotide sequence at least about 50%, 55%, 60%, 65%, 70%, 75%, 80%, 85%, 85%, 90%, 95%, 96%, 97%, 98%, 99% or more homologous or identical to the nucleotide sequence of SEQ ID NO:1, SEQ ID NO:3, SEQ ID NO:5, or SEQ ID NO:7.

Ranges intermediate to the above-recited values, e.g., isolated nucleic acid molecules comprising a nucleotide sequence which is about 20-60%, 60-70%, 70-80% or 80-90% identical to the amino acid sequence set forth in SEQ ID NO:1, SEQ ID NO:3, SEQ ID NO; 5, or SEQ ID NO:7 are also intended to be encompassed by the present invention. Values and ranges included and/or intermediate within the ranges set forth herein are also intended to be within the scope of the present invention. For example, isolated nucleic acid molecules comprising a nucleotide sequence which is about 91%, 92%, 93%, 94%, 95%, 96%, 97%, 98%, and 99% identical to the nucleotide sequence set forth in SEQ ID NO:1, SEQ ID NO:3, SEQ ID NO:5, or SEQ ID NO:7 are intended to be included within the range of about 90% identical to the nucleotide sequence set forth in SEQ ID NO:1, SEQ ID NO:3, SEQ ID NO:5, or SEQ ID NO:7.

In one embodiment of the invention, a promoter region (SEQ ID NO:7), or portion thereof, is operably linked to a non-native sequence. As used herein, the term "non-native" refers to any nucleic acid sequence including any RNA or DNA sequence, which is not normally associated with the seed-specific promoter. This includes heterologous nucleic acid sequences which are obtained from the same plant species as the promoter but are not associated with the promoter in the wild-type (non-transgenic) plant. In one embodiment, non-native genes of the invention include any gene associated with lipid biosynthesis and/or fatty acid biosynthesis, e.g., a desaturase.

In one embodiment of the invention, the non-native nucleic acid comprises any gene associated with lipid biosynthesis and/or fatty acid biosynthesis. Examples of genes involved in fatty acid biosynthesis include, but are not limited to, desaturases (e.g., a Δ15 desaturase). The gene of interest, including the examples set forth here, can be operatively linked to a promoter of the invention such that the gene of interest is expressed in developing seeds. In a preferred embodiment, the gene of interest is "plant derived." The term "plant-derived" or "derived-from", for example a plant, includes a gene product which is encoded by a plant gene.

The non-native nucleic acid sequence when linked to a seed-specific promoter from flax results in a chimeric or fusion product. The chimeric construct is introduced into a flax plant cell to create a transgenic flax plant cell which results in a detectably different phenotype of the flax plant cell or a flax plant grown from it when compared with a non-transgenic flax plant cell or flax plant grown from it. A contiguous nucleic acid sequence identical to the nucleic acid sequence of the chimeric construct is not present in the non-transformed flax plant cell or flax plant grown from it. In this respect, chimeric nucleic acid sequences include those sequences which contain a flax promoter linked to a nucleic acid sequence obtained from another plant species or a nucleic acid sequence from flax but normally not associated with that promoter. Chimeric nucleic acid sequences as used herein further include sequences comprising a flax promoter and a nucleic acid sequence that is normally linked to the promoter but additionally containing a non-native nucleic acid sequence. For example, if the promoter is a flax seed-specific omega-3 desaturase FAD3 promoter, sequences "non-native" to the flax omega-3 desaturase FAD3 promoter also include a sequence comprising a fusion between the flax omega-3 desaturase FAD3 gene naturally associated with the omega-3 desaturase promoter, and a coding sequence of interest that is not naturally associated with the promoter. The term non-native is also meant to include a fusion gene, which additionally includes a cleavage sequence separating the nucleic acid sequence that is normally linked to the promoter sequence and the gene encoding the protein of interest.

The term "seed-specific promoter," means that a gene expressed under the control of the promoter is predominantly expressed in plant seeds with no or no substantial expression, typically less than 5% of the overall expression level, in other plant tissues.

In one aspect of the invention, the present invention provides a novel flax seed specific promoter, or biologically active fragments thereof, useful for the expression of non-native genes in flax seeds and the seeds of other plant species. The promoters may be used to modify for example the protein, oil, or polysaccharide composition of the seeds.

In another aspect of the invention, the chimeric nucleic acid sequences can be incorporated in a known manner in a recombinant expression vector. Accordingly, the present invention includes a recombinant expression vector comprising a chimeric nucleic acid sequence of the present invention suitable for expression in a seed cell.

The term "suitable for expression in a seed cell" means that the recombinant expression vectors contain the chimeric nucleic acids sequence of the invention, a regulatory region, and a termination region, selected on the basis of the seed cell to be used for expression, which is operatively linked to the nucleic acid sequence encoding the polypeptide of the gene of interest. "Operatively linked" or "operably linked" are intended to mean that the chimeric nucleic acid sequence encoding the polypeptide is linked to a regulatory sequence and termination region which allows expression in the seed cell. A typical construct consists, in the 5' to 3' direction of a regulatory region complete with a promoter capable of directing expression in a plant, a polypeptide coding region, and a transcription termination region functional in plant cells. These constructs may be prepared in accordance with methodology well known to those of skill in the art of molecular biology (see for example: Sambrook et al. (1990), Molecular Cloning, 2nd ed. Cold Spring Harbor Press). The preparation of constructs may involve techniques such as restriction digestion, ligation, gel electrophoresis, DNA sequencing and PCR. A wide variety of cloning vectors is available to perform the necessary cloning steps. Especially suitable for this purpose are the cloning vectors with a replication system that is functional in *Escherichia coli* such as pBR322, the pUC series M13 mp series, pACYC184, pBluescript etc. Nucleic acid sequences may be introduced into these vectors and the vectors may be used to transform *E. coli* which may be grown in an appropriate medium. Plasmids may be recovered from the cells upon harvesting and lysing the cells. Final constructs may be introduced into plant vectors compatible with integration into the plant such as the Ti and Ri plasmids.

The methods for the expression of non-native genes in flax seeds in accordance with the present invention may be practiced using any flax seed-specific promoter and are not limited to the specific flax seed specific promoter that is described herein. In preferred embodiments of the present invention, the flax seed-specific promoter confers to the non-native nucleic acid sequence at least one phenotypic characteristic which is similar or identical to a phenotypic characteristic conferred to the native nucleic acid sequence by the native promoter. The term "phenotypic characteristic" or "phenotype" as used herein refers to any measurable property or effect conferred by the flax seed-specific promoter to the nucleic acid sequence operably linked to the flax seed-specific promoter. In one embodiment, timing of expression in the plant's life cycle, of the non-native nucleic acid sequence is similar or identical to timing of expression of the native nucleic acid sequence. In another embodiment, the expression level of the heterologous nucleic acid sequence is similar or identical to the expression level of the native nucleic acid sequence. Other desired expression characteristics conferred by a flax seed-specific promoter may be recognized by those skilled in the art and a flax seed-specific promoter may be selected accordingly.

Flax-seed specific promoters that may be used in accordance with the present invention include promoters associated with seed storage proteins, such as all albumins and globulins, including the vicilin and legumin-like proteins, as well as seed-specific promoters not associated with seed storage proteins, such as oleosins. Of further particular interest are promoters associated with fatty acid metabolism, such as acyl carrier protein (ACP), saturases, desaturases, and elongases.

In one feature of the invention, the flax FAD3 gene promoter is capable of controlling gene expression specifically during seed development. In one embodiment of the invention, the seed-specific promoter is the promoter sequence of LuFAD3B (SEQ ID NO:7), or a functional portion thereof (i.e., a portion capable of directing gene expression).

In still another embodiment of the invention, a promoter sequence is used which is at least about 60%, preferably about 70%, more preferably about 80%, and even more preferably about 90% or more identical to a promoter nucleotide sequence set forth in SEQ ID NO:7. In still another embodiment, a promoter sequence of the invention is used which hybridizes under stringent conditions to SEQ ID NO:7.

The gene of interest to be operatively linked to the promoter may be any nucleic acid sequence of interest including any RNA or DNA sequence encoding a peptide or protein of interest, for example, an enzyme, or a sequence complementary to a genomic sequence, where the genomic sequence may be at least one of an open reading frame, an intron, a non-coding leader sequence, or any sequence where the complementary sequence will inhibit transcription, messenger RNA processing, for example splicing or translation. The nucleic acid sequence of the gene of interest may be synthetic, naturally derived or a combination thereof. As well, the nucleic acid sequence of interest could be a fragment of the natural sequence, for example just include the catalytic domain or a structure of particular importance. The gene of interest might also be a recombinant protein. Depending upon the nature of the nucleic acid sequence of interest, it may be desirable to synthesize the sequence with plant preferred codons. The plant preferred codons may be determined from the codons of highest frequency in the proteins expressed in the largest amount in particular plant species of interest, and is known to one skilled in the art.

In one embodiment of the invention, the described seed-specific promoter can be operatively linked the gene of interest, particularly a desaturase, such that the gene of interest, or product thereof, is overexpressed and purified and/or extracted from the seed. One aspect of the present invention features culturing a cell containing the seed-specific promoter linked to the gene of interest. In this aspect the gene of interest is involved in lipid biosynthesis, and over expression of this gene leads to increased production in fatty acid biosynthesis.

The nucleotide sequence of the isolated LuFAD3B promoter region is shown in SEQ ID NO:7. The LuFAD3B promoter sequence is approximately 1130 nucleotides in length. The nucleotide sequence of the previously isolated flax LuFAD3A promoter is shown in SEQ ID NO:39. The LuFAD3A promoter is approximately 1,104 nucleotides in length. These promoters are each capable of controlling gene expression during seed development in flax. Alignment of the LuFAD3A and LuFAD3B promoters using Vector NTI software, a gap opening penalty of 15 and a gap extension penalty of 6.6 shows that the two sequences are approximately 75.3% identical.

The nucleotide sequence of the isolated LuFAD3B wild-type (Normandy) gene and the predicted amino acid sequence of the polypeptide or desaturase encoded by this gene are shown in SEQ ID NOs:5 and 6, respectively. The nucleotide of the LuFAD3B mutant allele (Solin) and the predicted amino acid sequence of the polypeptide encoded by this allele are shown in SEQ ID NOs:1 and 2, respectively. The nucleotide sequence of the LuFAD3A mutant allele (Solin) and the predicted amino acid sequence of the polypeptide encoded by this allele are shown in SEQ ID NOs:3 and 4, respectively.

Various aspects of the invention are described in further detail in the following subsections:

I. Isolated Nucleic Acid Molecules

One aspect of the invention pertains to isolated flax FAD3 (LuFAD3) nucleic acid molecules (i.e., Lu FAD3B Normandy type (SEQ ID NO:5), LuFAD3B Solin type (SEQ ID NO:1), LuFAD3A Solin type (SEQ ID NO:3), and LuFAD3B promoter (SEQ ID NO:7)) which can be used as biological markers. Another aspect of the invention pertains to isolated LuFAD3 nucleic acid molecules that encode LuFAD3B Normandy type polypeptides, or biologically active portions thereof. In another embodiment of the invention, isolated nucleic acids include the promoter region of the LuFAD3B gene (e.g., SEQ ID NO:7), or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated LuFAD3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:5, or SEQ ID NO:7, or a portion thereof, can be isolated using standard molecular biology techniques and the sequence information provided herein. Using all or a portion of the nucleic acid sequence of SEQ ID NO:1, SEQ ID NO:3, SEQ ID NO:5, or SEQ ID NO:7, as a hybridization probe, LuFAD3 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989). In another embodiment of the invention, the promoter region to LuFAD3B, including SEQ ID NO:7, or portions thereof, can be isolated using standard molecular biology techniques and the methods described above.

Moreover, a nucleic acid molecule encompassing all or a portion of SEQ ID NO:1, SEQ ID NO:3, SEQ ID NO:5, or SEQ ID NO:7 can be isolated by the polymerase chain reaction (PCR) using synthetic oligonucleotide primers designed based upon the sequence of SEQ ID NO:1, SEQ ID NO:3, SEQ ID NO:5, or SEQ ID NO:7.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to LuFAD3 nucleotide sequences, including the corresponding promoter region, can be prepared by standard synthetic techniques, e.g., using an automated DNA synthesizer.

In one embodiment, an isolated nucleic acid molecule of the invention comprises the nucleotide sequence shown in SEQ ID NO:1. The sequence of SEQ ID NO:1 corresponds to the mutant allele, LuFAD3B Solin cDNA. This cDNA comprises sequences encoding the LuFAD3B Solin polypeptide, as well as 5' untranslated sequences, and 3' untranslated sequences. In another embodiment, the nucleic acid molecule consists of the nucleotide sequence set forth as SEQ ID NO:1.

In another embodiment, an isolated nucleic acid molecule of the invention comprises the nucleotide sequence shown in SEQ ID NO:3. The sequence of SEQ ID NO:3 corresponds to the mutant allele, LuFAD3A Solin cDNA. This cDNA comprises sequences encoding the LuFAD3A Solin polypeptide, as well as 5' untranslated sequences, and 3' untranslated sequences. In another embodiment, the nucleic acid molecule consists of the nucleotide sequence set forth as SEQ ID NO:3.

In yet another embodiment, an isolated nucleic acid molecule of the invention comprises the nucleotide sequence shown in SEQ ID NO:5. The sequence of SEQ ID NO:7 corresponds to the wildtype LuFAD3B Normandy cDNA. This cDNA comprises sequences encoding the LuFAD3B desaturase polypeptide, as well as 5' untranslated sequences, and 3' untranslated sequences. In another embodiment, the nucleic acid molecule consists of the nucleotide sequence set forth as SEQ ID NO:5.

In still another embodiment, an isolated nucleic acid molecule of the invention comprises the nucleotide sequence shown in SEQ ID NO:7. The sequence of SEQ ID NO:7 corresponds to the LuFAD3B promoter. This promoter comprises approximately 1130 nucleotide bases. The LuFAD3B promoter is active in the developing seed, and is capable of controlling gene expression during seed development. In another embodiment, the nucleic acid molecule consists of the nucleotide sequence set forth as SEQ ID NO:7.

In still another embodiment, an isolated nucleic acid molecule of the invention comprises a nucleic acid molecule which is a complement of the nucleotide sequence shown in SEQ ID NO:1, SEQ ID NO:3, SEQ ID NO:5, and/or SEQ ID NO:7, or a portion of any of these nucleotide sequences. A nucleic acid molecule which is complementary to the nucleotide sequence shown in SEQ ID NO:1, SEQ ID NO:3, SEQ ID NO:5, or SEQ ID NO:7, is one which is sufficiently complementary to the nucleotide sequence shown in SEQ ID NO:1, SEQ ID NO:3, SEQ ID NO:5, or SEQ ID NO:7, such that it can hybridize to the nucleotide sequence shown in SEQ ID NO:1, SEQ ID NO:3, SEQ ID NO:5, or SEQ ID NO:7, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the nucleotide sequence shown in SEQ ID NO:1, SEQ ID NO:3, SEQ ID NO:5, or SEQ ID NO:7 (e.g., to the entire length of the nucleotide sequence), or a portion of any of these nucleotide sequences. In one embodiment, a nucleic acid molecule of the present invention comprises a nucleotide sequence which is at least (or no greater than) 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and hybridizes under stringent hybridization conditions to a complement of a nucleic acid molecule of SEQ ID NO:1, SEQ ID NO:3, SEQ ID NO:5, or SEQ ID NO:7.

Moreover, the nucleic acid molecule of the invention can comprise only a portion of the nucleic acid sequence of SEQ ID NO:5 or SEQ ID NO:7, for example, a fragment which can be used as a probe or primer or a fragment encoding a portion of a LuFAD3 polypeptide or promoter, e.g., a biologically active portion of a LuFAD3 desaturase polypeptide or a biologically active portion of a LuFAD3 promoter which is capable of directing seed-specific gene expression. The nucleotide sequences determined from the cloning of the LuFAD3 genes and promoter region allows for the generation of probes and primers designed for use in identifying and/or cloning other LuFAD3 family members, as well as homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:5 or SEQ ID NO:7 of an anti-sense sequence of SEQ ID NO:5 or SEQ ID NO:7, or of a naturally occurring allelic variant or mutant of SEQ ID NO:5 or SEQ ID NO:7.

Exemplary probes or primers are at least 12, 15, 20, 25, 30, 35, 40, 45, 50, 55, 60, 65, 70, 75 or more nucleotides in length and/or comprise consecutive nucleotides of an isolated nucleic acid molecule described herein. Probes based on the LuFAD3 nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a LuFAD3 sequence, e.g., a domain, region, site or other sequence described herein. The primers should be at least 5, 10, 20, 30, 40, 50, 60, 70, 80, 90, 100 or more nucleotides in length. Such probes can be used as a part of a diagnostic test kit for identifying cells or tissue which misexpress a LuFAD3 polypeptide, such as by measuring a level of a LuFAD3-encoding nucleic acid in a sample of cells from a subject, e.g., detecting Lu4FAD3 mRNA levels or determining whether a genomic LuFAD3 gene has been mutated or deleted.

A nucleic acid fragment encoding a "biologically active portion of a wildtype (Normandy) LuFAD3B polypeptide" can be prepared by isolating a portion of the nucleotide sequence of SEQ ID NO:5 which encodes a polypeptide having a LuFAD3 biological activity, expressing the encoded portion of the LuFAD3 polypeptide (e.g., by recombinant expression in vitro) and assessing the activity of the encoded portion of the LuFAD3 polypeptide. In an exemplary embodiment, the nucleic acid molecule is at least 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and encodes a polypeptide having a LuFAD3 activity (as described herein). In another exemplary embodiment, the nucleic acid molecule is at least 50-100, 100-250, 250-500, 500-750, 750-1000, 1000-1250, 1250-1500, 1500-1750, 1750-1850 or more nucleotides in length and encodes a polypeptide having desaturase activity.

In another embodiment, the invention features a nucleic acid fragment or portion of the LuFAD3B promoter sequences shown SEQ ID NO:7. A fragment of a promoter of the invention is any fragment which is capable of controlling expression of the gene which is operatively linked in a developing seed. In an exemplary embodiment, the nucleic acid molecule is at least 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and encodes a promoter having LuFAD3 promoter activity (as described herein). In another exemplary embodiment, the nucleic acid molecule is at least 50-100, 100-250, 250-500, 500-750, 750-1000, 1000-1250, 1250-1500, 1500-1750, 1750-1850 or more nucleotides in length and encodes a promoter having LuFAD3 promoter activity (as described herein).

The invention further encompasses nucleic acid molecules that differ from the nucleotide sequence shown in SEQ ID NO:5 or SEQ ID NO:7. Such differences can be due to due to degeneracy of the genetic code, thus resulting in a nucleic acid which encodes the same LuFAD3 polypeptide or promoter as those encoded by the nucleotide sequence shown in SEQ ID NO:5 or SEQ ID NO:7. In another embodiment, an isolated nucleic acid molecule of the invention has a nucleotide sequence encoding a polypeptide having an amino acid sequence which differs by at least 1, but no greater than 5, 10, 20, 50 or 100 amino acid residues from the amino acid sequence shown in SEQ ID NO:6. In yet another embodiment, the nucleic acid molecule encodes the amino acid sequence of SEQ ID NO:6. If an alignment is needed for this comparison, the sequences should be aligned for maximum homology.

Nucleic acid variants can be naturally occurring, such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the flax population) that lead to changes in the amino acid sequences of the LuFAD3 polypeptides. Such genetic polymorphism in the LuFAD3 genes may exist among individuals within a population due to natural allelic variation. As used herein, the terms "gene" and "recombinant gene" refer to nucleic acid molecules which include an open reading frame encoding a LuFAD3 polypeptide, preferably a plant LuFAD3 polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:6, for example, allelic variants comprising the nucleotide sequence shown in SEQ ID NO:1, or encoding a polypeptide having the amino acid sequence shown in SEQ ID NO:2. In another aspect, the invention features isolated nucleic acid molecules which encode a naturally occurring allelic variant of a polypeptide comprising the amino acid sequence of SEQ ID NO:6, wherein the nucleic acid molecule hybridizes to a complement of a nucleic acid molecule comprising SEQ ID NO:5, for example, under stringent hybridization conditions.

Allelic variants of wildtype LuFAD3 include both functional and non-functional LuFAD3 polypeptides. Functional allelic variants are naturally occurring amino acid sequence variants of the LuFAD3 polypeptide that have a LuFAD3 activity, e.g., maintain the ability to bind a LuFAD3 substrate and/or modulate the formation of double bounds. Functional allelic variants will typically contain only conservative substitution of one or more amino acids of SEQ ID NO:6, or substitution, deletion or insertion of non-critical residues in non-critical regions of the polypeptide.

Non-functional allelic variants are naturally occurring amino acid sequence variants of the LuFAD3 polypeptide that do not have a LuFAD3 activity, e.g., they do not have the ability to introduce a double bond into a fatty acid. Non-functional allelic variants will typically contain a non-conservative substitution, a deletion, or insertion or premature truncation of the amino acid sequence of SEQ ID NO:6, or a substitution, insertion or deletion in critical residues or critical regions. Examples of such non-functional allelic variants include polypeptides comprising the amino acid sequence shown in SEQ ID NO:2.

The present invention further provides non-flax orthologues of the LuFAD3 polypeptides. Orthologues of LuFAD3 polypeptides are polypeptides that are isolated from non-flax organisms and possess the same LuFAD3 activity, e.g., ability to introduce double bonds into a fatty acid, as the LuFAD3 polypeptide. Orthologues of the LuFAD3 polypeptide can readily be identified as comprising an amino acid sequence that is substantially identical to SEQ ID NO:6.

Moreover, nucleic acid molecules encoding other LuFAD3 family members and, thus, which have a nucleotide sequence which differs from the LuFAD3 sequences of SEQ ID NO:1, SEQ ID NO:3, SEQ ID NO:5, or SEQ ID NO:7 are intended to be within the scope of the invention. For example, another LuFAD3 cDNA can be identified based on the nucleotide sequence of LuFAD3. Moreover, nucleic acid molecules encoding LuFAD3 polypeptides from different species, and which, thus, have a nucleotide sequence which differs from the LuFAD3 sequences of SEQ ID NO:1, SEQ ID NO:3, SEQ ID NO:5, or SEQ ID NO:7 are intended to be within the scope of the invention.

Nucleic acid molecules corresponding to natural allelic variants and homologues of the LuFAD3 cDNAs of the invention can be isolated based on their homology to the LuFAD3 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the LuFAD3 cDNAs of the invention can further be isolated by mapping to the same chromosome or locus as the LuFAD3 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:5, or SEQ ID NO:7. In other embodiment, the nucleic acid is at least 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2500, 2500-3000, 3000-3500 or more nucleotides in length. In other embodiment, the nucleic acid is at least 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS).

Preferably, an isolated nucleic acid molecule of the invention that hybridizes under stringent conditions to the sequence of SEQ ID NO:1, SEQ ID NO:3, SEQ ID NO:5, or SEQ ID NO:7 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the LuFAD3 sequences that may exist in the population, the skilled artisan will further appreciate that changes can be introduced by mutation into the nucleotide sequence of SEQ ID NO:5, thereby leading to changes in the amino acid sequence of the encoded LuFAD3 polypeptides, without altering the functional ability of the LuFAD3 polypeptides. For example, nucleotide substitutions leading to amino acid substitutions at "non-essential" amino acid residues can be made in the sequence of SEQ ID NO:5. A "non-essential" amino acid residue is a residue that can be altered from the wild-type sequence of LuFAD3 (e.g., the sequence of SEQ ID NO:6) without altering the biological activity, whereas an "essential" amino acid residue is required for biological activity. Furthermore, additional amino acid residues that are conserved between the LuFAD3 polypeptides of the present invention and other members of the LuFAD3 family are not likely to be amenable to alteration.

Accordingly, another aspect of the invention pertains to nucleic acid molecules encoding LuFAD3 polypeptides that contain changes in amino acid residues that are not essential for activity. Such LuFAD3 polypeptides differ in amino acid sequence from SEQ ID NO:6, yet retain biological activity. In one embodiment, the isolated nucleic acid molecule comprises a nucleotide sequence encoding a polypeptide, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:6. In another embodiment, the isolated nucleic acid molecule comprises a nucleotide sequence encoding a promoter region, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:7.

An isolated nucleic acid molecule encoding a LuFAD3 polypeptide identical to the polypeptide of SEQ ID NO:6 can be created by introducing one or more nucleotide substitutions, additions or deletions into the nucleotide sequence of SEQ ID NO:5 such that one or more amino acid substitutions, additions or deletions are introduced into the encoded polypeptide. Mutations can be introduced into SEQ ID NO:5 such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted non-essential amino acid residue in a LuFAD3 polypeptide is preferably replaced with another amino acid residue from the same side chain family. Alternatively, in another embodiment, mutations can be introduced randomly along all or part of a LuFAD3 coding sequence, such as by saturation mutagenesis, and the resultant mutants can be screened for LuFAD3 biological activity to identify mutants that retain activity. Following mutagenesis of SEQ ID NO:5, the encoded polypeptide can be expressed recombinantly and the activity of the polypeptide can be determined.

In addition to the nucleic acid molecules encoding LuFAD3 polypeptides described above, as well as the promoter regions of these genes, another aspect of the invention pertains to isolated nucleic acid molecules which are antisense thereto. In an exemplary embodiment, the invention provides an isolated nucleic acid molecule which is antisense to a LuFAD3B nucleic acid molecule (e.g., is antisense to the coding strand of a wildtype LuFAD3B nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LuFAD3B coding strand, or to only a portion thereof. In one embodiment, an antisense nucleic acid molecule is antisense to a "coding region" of the coding strand of a nucleotide sequence encoding LuFAD3. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding LuFAD3B. The term "noncoding region" refers to 5' and 3' sequences which flank the coding region that are not translated into amino acids (i.e., also referred to as 5' and 3' untranslated regions).

Given the coding strand sequences encoding LuFAD3B disclosed herein, antisense nucleic acids of the invention can be designed according to the rules of Watson and Crick base pairing. Similar methods can be applied to the promoters described in the invention, whereby antisense molecules interfere with specific control regions within the promoter. The antisense nucleic acid molecule can be complementary to the entire coding region of LuFAD3B mRNA, but more preferably is an oligonucleotide which is antisense to only a portion of the coding or noncoding region of LuFAD3B mRNA. For example, the antisense oligonucleotide can be complementary to the region surrounding the translation start site of LuFAD3B mRNA (e.g., between the −10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically generated in situ such that they hybridize with or bind to cellular mRNA and/or genomic DNA encoding a LuFAD3B polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells. For example, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intra-cellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave LuFAD3B mRNA transcripts to thereby inhibit translation of LuFAD3B mRNA. A ribozyme having specificity for a LuFAD3B-encoding nucleic acid can be designed based upon the nucleotide sequence of a LuFAD3B cDNA disclosed herein (i.e., SEQ ID NO:5). For example, a derivative of a Tetrahymena L-19 IVS RNA can be constructed in which the nucleotide sequence of the active site is complementary to the nucleotide sequence to be cleaved in a LuFAD3B-encoding mRNA. See, e.g., Cech et al. U.S. Pat. No. 4,987,071; and Cech et al. U.S. Pat. No. 5,116,742. Alternatively, LuFAD3B mRNA can be used to select a catalytic RNA having a specific ribonuclease activity from a pool of RNA molecules. See, e.g., Bartel, D. and Szostak, J. W. (1993) *Science* 261:1411-1418.

Alternatively, LuFAD3B gene expression can be inhibited by targeting nucleotide sequences complementary to the regulatory region of the LuFAD3B (e.g., the LuFAD3 promoter and/or enhancers) to form triple helical structures that prevent transcription of the LuFAD3 gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In yet another embodiment, the LuFAD3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670-675.

PNAs of LuFAD3B nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of LuFAD3B nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of LuFAD3B can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of LuFAD3B nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous LuFAD3B gene within a cell line or microorganism may be modified by inserting a heterologous DNA regulatory element into the genome of a stable cell line or cloned microorganism such that the inserted regulatory element is operatively linked with the endogenous LuFAD3B gene. For example, an endogenous LuFAD3B gene which is normally "transcriptionally silent", i.e., a LuFAD3B gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous LuFAD3B gene may be activated by insertion of a promiscuous regulatory element that works across cell types.

A heterologous regulatory element may be inserted into a stable cell line or cloned microorganism, such that it is operatively linked with an endogenous LuFAD3B gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated Polypeptides

One aspect of the invention pertains to isolated LuFAD3 or recombinant polypeptides and polypeptides, and biologically active portions thereof, as well as polypeptide fragments suitable for use as immunogens to raise LuFAD3 antibodies. In one embodiment, native LuFAD3 polypeptides can be isolated from cells or tissue sources by an appropriate purification scheme using standard protein purification techniques. In another embodiment, LuFAD3 polypeptides are produced by recombinant DNA techniques. Alternative to recombinant expression, a LuFAD3 polypeptide or polypeptide can be synthesized chemically using standard peptide synthesis techniques.

An "isolated" or "purified" polypeptide or biologically active portion thereof is substantially free of cellular material or other contaminating proteins from the cell or tissue source from which the LuFAD3 polypeptide is derived, or substantially free from chemical precursors or other chemicals when chemically synthesized. The language "substantially free of cellular material" includes preparations of LuFAD3 polypeptide in which the polypeptide is separated from cellular components of the cells from which it is isolated or recombinantly produced. In one embodiment, the language "substantially free of cellular material" includes preparations of LuFAD3 polypeptide having less than about 30% (by dry weight) of non-LuFAD3 polypeptide (also referred to herein as a "contaminating protein"), more preferably less than about 20% of LuFAD3 polypeptide, still more preferably less than about 10% of non-LuFAD3 polypeptide, and most preferably less than about 5% non-LuFAD3 polypeptide. When the LuFAD3 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of LuFAD3 polypeptide in which the polypeptide is separated from chemical precursors or other chemicals which are involved in the synthesis of the polypeptide. In one embodiment, the language "substantially free of chemical precursors or other chemicals" includes preparations of LuFAD3 polypeptide having less than about 30% (by dry weight) of chemical precursors or non-LuFAD3 chemicals, more preferably less than about 20% chemical precursors or non-LuFAD3 chemicals, still more preferably less than about 10% chemical precursors or non-LuFAD3 chemicals, and most preferably less than about 5% chemical precursors or non-LuFAD3 chemicals.

As used herein, a "biologically active portion" of a LuFAD3 polypeptide includes a fragment of a LuFAD3B polypeptide which participates in an interaction between a LuFAD3 molecule and a non-LuFAD3 molecule. Biologically active portions of a LuFAD3 polypeptide include peptides comprising amino acid sequences sufficiently identical to or derived from the amino acid sequence of the wildtype LuFAD3B polypeptide, e.g., the amino acid sequence shown in SEQ ID NO:6, which include less amino acids than the full length wildtype LuFAD3B polypeptides, and exhibit at least one activity of a wildtype LuFAD3B polypeptide, e.g., modulating double bonds in fatty acids. A biologically active portion of a wildtype LuFAD3B polypeptide can be a polypeptide which is, for example, 25, 30, 35, 40, 45, 50, 75, 100, 125, 150, 175, 200, 225, 250, 275, 300, 325, 350, 375 or more amino acids in length. Biologically active portions of a wildtype LuFAD3B polypeptide can be used as targets for developing agents which modulate a LuFAD3B mediated activity, e.g., modulating double bonds in fatty acids.

Another aspect of the invention features fragments of the polypeptide having the amino acid sequence of SEQ ID NO:6, for example, for use as immunogens. In one embodiment, a fragment comprises at least 5 amino acids (e.g., contiguous or consecutive amino acids) of the amino acid sequence of SEQ ID NO:6. In another embodiment, a fragment comprises at least 10, 15, 20, 25, 30, 35, 40, 45, 50 or more amino acids (e.g., contiguous or consecutive amino acids) of the amino acid sequence of SEQ ID NO:6.

In a preferred embodiment, a LuFAD3 polypeptide has an amino acid sequence shown in SEQ ID NO:6. In other embodiments, the LuFAD3 polypeptide is substantially identical to SEQ ID NO:6, and retains the functional activity of the polypeptide of SEQ ID NO:6, yet differs in amino acid sequence due to natural allelic variation or mutagenesis, as described in detail in subsection I above. In another embodiment, the LuFAD3 polypeptide is a polypeptide which comprises an amino acid sequence at least about 50%, 55%, 60%, 65%, 70%, 75%, 80%, 85%, 90%, 95%, 96%, 97%, 98%, 99% or more identical to SEQ ID NO:6.

In another embodiment, the invention features a LuFAD3 polypeptide which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:5, or a complement thereof. This invention further features a LuFAD3 polypeptide which is encoded by a nucleic acid molecule consisting of a nucleotide sequence which hybridizes under stringent hybridization conditions to a complement of a nucleic acid molecule comprising the nucleotide sequence of SEQ ID NO:5, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11-17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to LuFAD3 nucleic acid molecules of the invention. BLAST protein searches can be performed with the XBLAST program, score=100, wordlength=3, and a Blosum62 matrix to obtain amino acid sequences homologous to LuFAD3 polypeptide molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm.nih.gov.

The invention also provides LuFAD3 chimeric or fusion proteins. As used herein, a LuFAD3 "chimeric protein" or "fusion protein" comprises a wildtype LuFAD3B polypeptide operatively linked to a non-LuFAD3 polypeptide. A "non-LuFAD3 polypeptide" refers to a polypeptide having an amino acid sequence corresponding to a polypeptide which is not substantially homologous to the LuFAD3 polypeptides, e.g., a polypeptide which is different from the LuFAD3B polypeptide and which is derived from the same or a different organism. Within a LuFAD3 fusion protein the LuFAD3B polypeptide can correspond to all or a portion of a LuFAD3B polypeptide. In a preferred embodiment, a LuFAD3B fusion protein comprises at least one biologically active portion of a LuFAD3B polypeptide. In another preferred embodiment, a LuFAD3B fusion protein comprises at least two biologically active portions of a LuFAD3B polypeptide. Within the fusion protein, the term "operatively linked" is intended to indicate that the LuFAD3B polypeptide and the non-LuFAD3 polypeptide are fused in-frame to each other. The non-LuFAD3 polypeptide can be fused to the N-terminus or C-terminus of the LuFAD3B polypeptide.

For example, in one embodiment, the fusion protein is a GST-LuFAD3 fusion protein in which the LuFAD3 sequence are fused to the C-terminus of the GST sequences. Such fusion proteins can facilitate the purification of recombinant LuFAD3.

In another embodiment, the fusion protein is a wildtype LuFAD3B polypeptide containing a heterologous signal sequence at its N-terminus. In certain host cells (e.g., mammalian host cells), expression and/or secretion of LuFAD3 can be increased through the use of a heterologous signal sequence.

III. Transgenic Plants

In another embodiment, the invention provides transgenic plants containing nucleic acids of the invention. In one embodiment, the transgenic plant contains the nucleotide sequence encoding the wildtype LuFAD3B polypeptides of the invention. In another embodiment, the invention further describes transgenic plants containing promoter sequences of LuFAD3B operatively linked to a gene of interest, preferably a gene involved in lipid biosynthesis. In order to introduce nucleic acid sequences into plant cells in general a variety of techniques are available to the skilled artisan. *Agrobacterium*-mediated transformation for flax plant cells has been reported and flax transformants may be obtained in accordance with the methods taught by Dong and McHughen (1993) Plant Science 88: 61-77, although a variety of other techniques may also be used to introduce the chimeric DNA constructs in flax cells if so desired.

Transformed flax plants grown in accordance with conventional agricultural practices known to a person skilled in the art are allowed to set seed. Flax seed may then be obtained from mature flax plants and analyzed for desired altered properties with respect to the wild-type seed.

Two or more generations of plants may be grown and either crossed or selfed to allow identification of plants and strains with desired phenotypic characteristics including production of the recombinant polypeptide. It may be desirable to ensure homozygosity in the plants to assure continued inheritance of the recombinant trait. Methods for selecting homozygous plants are well known to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means (e.g. treatment with colchicine or other microtubule disrupting agents).

Furthermore, a variety of techniques are available for the introduction of nucleic acid sequences, in particular DNA, into plant host cells in general. For example, the chimeric DNA constructs may be introduced into host cells obtained from dicotelydenous plants, such as tobacco, and oleoagenous species, such as *Brassica napus* using standard *Agrobacterium* vectors by a transformation protocol such as described by Moloney et al. (1989), Plant Cell Rep. 8: 238-242 or Hinchee et al. (1988) Bio/Technol. 6: 915-922; or other techniques known to those skilled in the art. For example, the use of T-DNA for transformation of plant cells has received extensive study and is amply described in EP 0 120 516, Hoekema et al., (1985), Chapter V In: *The Binary Plant Vector System* Offset-drukkerij Kanters BV, Alblasserdam); Knauf et al. (1983), *Genetic Analysis of Host Expression by Agrobacterium*, p. 245, In: *Molecular Genetics of Bacteria-Plant Interaction*, Puhler, A. ed. Springer-Verlag, NY); and An et al., (1985), (EMBO J., 4: 277-284). *Agrobacterium* transformation may also be used to transform monocot plant species (U.S. Pat. No. 5,591,616).

Explants may be cultivated with *Agrobacterium tumefaciens* or *Agrobacterium rhizogenes* to allow for the transfer of the transcription construct in the plant host cell. Following transformation using *Agrobacterium* the plant cells are dispersed into an appropriate medium for selection, subsequently callus, shoots and eventually plants are recovered. The *Agrobacterium* host will harbor a plasmid comprising the vir genes necessary for transfer of the T-DNA to plant cells. For injection and electroporation (see below) disarmed Ti-plasmids (lacking the tumor genes, particularly the T-DNA region) may be introduced into the plant cell.

The use of non-*Agrobacterium* techniques permits the use of constructs described herein to obtain transformation and expression in a wide variety of monocotyledonous and dicotyledonous plant species. These techniques are especially useful for transformation of plant species that are intractable in an *Agrobacterium* transformation system. Other techniques for gene transfer include particle bombardment (Sanford, (1988), Trends in Biotechn. 6: 299-302), electroporation (Fromm et al., (1985), PNAS USA, 82: 5824-5828; Riggs and Bates, (1986), PNAS USA 83: 5602-5606), PEG mediated DNA uptake (Potrykus et al., (1985), Mol. Gen. Genetics., 199: 169-177), microinjection (Reich et al., Bio/Techn. (1986) 4:1001-1004) and silicone carbide whiskers (Kaeppler et al. (1990) Plant Cell Rep. 9: 415-418).

In a further specific applications such as to *B. napus*, the host cells targeted to receive recombinant DNA constructs typically will be derived from cotyledonary petioles as described by Moloney et al. (1989) Plant Cell Rep. 8: 238-242. Other examples using commercial oil seeds include cotyledon transformation in soybean explants (Hinchee et al., (1988) Bio/Technol. 6: 915-922) and stem transformation of cotton (Umbeck et al., (1987) Bio/Technol. 5: 263-266).

Following transformation, the cells, for example as leaf discs, are grown in selective medium. Once the shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, to show integration into the genome of the host cell.

The methods provided by the present invention can be used in conjunction a broad range of plant species. Particularly preferred plant cells employed in accordance with the present invention include cells from the following plants: soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalfa (*Medicago sativa*), wheat (*Triticum* sp.), barley (*Hordeum vulgare*), oats (*Avena sativa* L.), sorghum (*Sorghum bicolor*), *Arabidopsis thaliana*, potato (*Solanum* sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

Another embodiment of the invention includes a transgenic plant containing a transgene comprising a nucleic acid containing a seed-specific promoter which is operatively linked to a gene of interest, preferably a gene involved in lipid biosynthesis. In a preferred embodiment of the invention, the transgenic plant produces fatty acids which can then be isolated and/or purified according to the methods described previously.

This invention is further illustrated by the following examples which should not be construed as limiting. The contents of all references, patents and published patent applications cited throughout this application are incorporated herein by reference.

EXAMPLES

General Methodology

Plant Material

Linseed flax cultivars CDC Normandy and Solin 93-708 were used for all experiments. Plants were grown in a growth chamber under standard conditions.

Isolation of Normandy LuFAD3A cDNA

The isolation of a flax FAD3 cDNA is described by Qiu et al., 2003, WO 02102970. The gene this cDNA represents will be referred to as LuFAD3A to distinguish it from the second gene described here and referred to as LuFAD3B.

Example 1

Identification of a Second LuFAD3 Gene

PCR amplification of genomic DNA with a number of primer sets based on the Normandy cDNA sequence produced two bands instead of the expected single band, suggesting the presence of a second, highly related gene. The products amplified with the primers Fex4F3 and Fex6R4 were cloned and sequenced, and regions within the coding region of Exon 5 that were variable between the two amplification products were identified. The sequences of Fex4F3 and Fex6R4 are set forth in SEQ ID NOs:8 and 9. Based on the sequences amplified with these primers, the primers, FLcDNAF and FLcDNAR, were designed which are specific to the LuFAD3B gene. The sequences of FLcDNAF and FLcDNAR are set forth in SEQ ID NOs:10 and 11.

Example 2

Solin Marathon cDNA Library

Solin flax seed was collected at 15-20 days after flowering (DAF), removed from the pod, frozen in liquid nitrogen, and ground to a fine powder. RNA was extracted according to the method described by Carpenter and Simon (1998) (Preparation of RNA In Methods in Molecular Biology, Vol. 82. *Arabidopsis* protocols (Edited by J. M. Martinez-Zapater and J. Salinas, Humana Press Inc., Totowa, N.J. pp. 85-98). Poly-A$^+$ RNA was isolated using a PolyAtract mRNA Isolation System III (Promega) according to the manufacturer's instructions. Adaptor-ligated cDNA was produced using the Marathon cDNA Amplification Kit (BD Biosciences Clontech) according to the manufacturer's instructions.

Example 3

Isolation of LUFAD3 Sequences from Solin

The Marathon (BD Biosciences Clontech) primer AP1 (5'-CCATCCTAATACGACTCACTATAGGGC-3') (SEQ ID NO:12) was used with primers FLcDNAR and FLcDNAF to obtain the 3' and 5' regions of the LuFAD3B cDNA from the Solin cDNA library. Each PCR reaction contained 5 μL of a 1:50 dilution of Solin cDNA, 10 pmol each primer, 1 μL dNTP mix (each at 10 mM) 5 μL 10×SA PCR reaction buffer (BD Biosciences Clontech) and 1 μL 50× Advantage 2 Polymerase Mix (BD Biosciences Clontech) in a total volume of 50 μL. The PCR cycle consisted of a 94° C. denaturation step for 1 min, 5 cycles of 94 for 30 s and 72 for 4 min, 5 cycles of 94° C. for 30 seconds (s) and 70° C. for 4 minutes (min) and 25 cycles of 94° C. for 30 s and 68° C. for 4 min. With AP1/FLcDNAR, a band of about 750 bp was produced whereas with AP1/FLcDNAF, an amplification product of about 900 bp was obtained. These bands were cloned into PCR4-TOPO (Invitrogen, Carlsbad, Calif.) and sequenced. The sequences had a 45 bp overlap, and the aligned sequences are set forth as the 1536 bp SEQ ID NO:1. The deduced translation product is set forth as SEQ ID NO:2.

The Marathon primer AP1 was used with primers Fex1F1 and Fex5R3 to obtain the 5' and 3' regions of the LuFAD3A gene from the Solin cDNA library. The sequences of Fex1F1 and Fex5R3 are set forth in SEQ ID NOs:13 and 14. The PCR conditions were the same as those used for the LuFAD3B cDNA. With AP1/FexF1, an amplification product of approximately 1000 bp was obtained and with AP1/Fex5R3, an amplification product of approximately 1430 bp was obtained. These bands were cloned into PCR4-TOPO (Invitrogen, Carlsbad, Calif.) and sequenced. The sequences had a 566 bp overlap, and alignment of these sequences produced a 1473 bp which is set forth as SEQ ID NO:3. The translation product of this sequence is set forth as SEQ ID NO:4.

Example 4

Isolation of LuFAD3B Sequences from Normandy

To amplify the LuFAD3B sequences from Normandy, the Normandy cDNA library was used as a template with the primer sets FLcDNAF and T7 (5'-CGGGATATCACTCAG-CATAATG-3') (SEQ ID NO:15) and FLcDNAR and T3 (5'-AATTAACCCTCACTAAAGGG-3') (SEQ ID NO:16). The hybridization positions for the T7 and T3 primers are located within the UniZap XR vector, at either end of the insert. Each PCR reaction contained 50 pmol of each primer, 5 μL Stratagene PfuUltra 10× Reaction Buffer, 1.0 μL dNTP mix (each at 10 mM), 2.5 U Stratagene PfuUltra DNA Polymerase and 5 μL of a 1:10 dilution of a phagemid stock of the library in a total volume of 50 μL. The PCR program consisted of a 4 min denaturation cycle at 94° C., followed by 30 cycles of 94° C. for 45 s, 58° C. for 30 s and 72° C. for 2 min, followed by a 10 min extension at 72° C. A second 10 min extension at 72° C. was performed after the addition of 2.5 U of Invitrogen Taq DNA polymerase. Reactions were run on a 0.8% agarose gel and gel purified. An amplification product of about 450 bp was obtained with the primer set FLcDNAR/T3, and a product of about 880 bp was obtained with FLcDNAF/T7. Fragments were cloned into PCR4-TOPO (Invitrogen, Carlsbad, Calif.) and sequenced, producing overlapping insert sequences. However, the sequences did not contain the 5' end of the gene. Therefore, the primer set Lu15bFLF/Lu15bFLR, based on the 5' end of the Solin LuFAD3B cDNA and the 3' ends of the Solin and Normandy B cDNAs was used to in a third PCR reaction with the UniZap cDNA library as a template. The sequences of Lu15bFLF and Lu15bFLR are set forth in SEQ ID NOs:17 and 18. PCR conditions and cloning were as described above. The three overlapping sequences were aligned to produce a 1495 bp sequence which is set forth as SEQ ID NO:5. The 391 amino acid translation product of this sequence is set forth as SEQ ID NO:6.

TABLE 1

| Source | Gene | cDNA Sequence | Amino Acid Sequence |
|---|---|---|---|
| Normandy | LuFAD3B | SEQ ID NO:5 | SEQ ID NO:6 |
| Solin | LuFAD3A | SEQ ID NO:3 | SEQ ID NO:4 |
| Solin | LuFAD3B | SEQ ID NO:1 | SEQ ID NO:2 |

The Normandy LuFAD3A (Xiao et al. (2003)) and LuFAD3B cDNA sequences shared 94.8% identity in the coding region at the nucleotide level, and 95.4% identity at the amino acid level. When compared to the Normandy LuFAD3A sequence, the Solin LuFAD3A cDNA sequence contained a single nucleotide substitution 873 nucleotides from the translational start, converting an arginine codon (CGA) to a stop codon (TGA). The Solin LuFAD3B sequence also carries a single nucleotide substitution, 143 nucleotides from the start site, converting a tryptophan codon (TGG) to a stop codon (TGA).

Example 5

Isolation of Solin Genomic Clones Containing the Mutated Regions

To reconfirm the presence and position of the point mutations in the Solin genes, the primer set NcDNAbEndR/Lu15bFLF was used to amplify the genomic region carrying the mutation in the LuFAD3B gene and the primer set Lu15AMutF/Lu15AMutR was used for the LuFAD3A gene. NcDNAbEndR, Lu15AMutF and Lu15AMutR are set forth as SEQ ID NOs:19, 20, and 21. Genomic DNA was isolated from young leaves and cotyledons of Solin using a DNAesy maxi kit according to the manufacturers' instructions. The PCR reaction included 50 pmol of each primer, 5 µL Stratagene PfuUltra 10× Reaction Buffer, 1.0 µL dNTP mix (each at 10 mM), 2.5 U Stratagene PfuUltra DNA Polymerase and approximately 100 ng genomic DNA in a volume of 50 µL. The PCR program consisted of a 4 min denaturation cycle at 94° C., followed by 25 cycles of 94° C. for 45 s, 61° C. for 30 s and 72° C. for 2 min, and a final 10 min extension at 72° C. Inserts were cloned into the vector PCR4-TOPO and sequenced. The insert sequence for the LuFAD3A gene is set forth as SEQ ID NO:22 the insert sequence for the LuFAD3B gene is set forth as SEQ ID NO:23. The identical point mutations that were found in the cDNA sequences were identified in the genomic clones.

Example 6

Yeast Expression Plasmids

The sequence around the translational start sites of the LuFAD3A and LuFAD3B are very similar. Therefore, prior to cloning the coding regions for expression in yeast, the primer sets Lu15bFLF/Lu15bFLR and Lu15aFLF/Lu15AYR were used to amplify the full-length LuFAD3A and LuFAD3B cDNAs from Solin and Normandy. The sequences of Lu15aFLF and Lu15AYR are set forth in SEQ ID NOs:24 and 25. The Marathon cDNA library was used as the template for the Solin clones. First-strand cDNA from seed RNA reverse-transcribed with the SuperScript First-Strand Synthesis System for RT-PCR (Invitrogen, Carlsbad, Calif.) was used as a template for the Normandy full-length LuFAD3A clone. PCR fragments were cloned in PCR4-TOPO.

For expression in yeast, the coding region of each of the four full-length plasmids was amplified using the primer set Lu15AYR/Lu15BYF for LuFAD3A clones, and Lu15BYR/Lu15BYF for LuFAD3B clones. The sequences of Lu15BYF and Lu15BYR are set forth in SEQ ID NOs:26 and 27.

Each PCR reaction contained 50 pmol of each primer, 5 µL Stratagene PfuUltra 10× Reaction Buffer, 1.0 µL dNTP mix (each at 10 mM), 2.5 U Stratagene PfuUltra DNA Polymerase and approximately 300 ng of the appropriate plasmid in a total volume of 50 µL. The PCR program consisted of a 4 min denaturation cycle at 94° C., followed by 30 cycles of 94° C. for 45 s, 58° C. for 30 s and 72° C. for 2 min, followed by a 10 min extension at 72° C. A second 10 min extension at 72° C. was performed after the addition of 2.5 U of Invitrogen Taq DNA polymerase. Reactions were run on a 0.8% agarose gel, and amplification products were gel purified using a Qiagen QiaexII Gel Extraction kit according to the manufacturer's instructions. Isolated fragments were cloned into the yeast expression vector pYES2.1/V5-His-TOPO (Invitrogen, Carlsbad, Calif.) according to the manufacturer's instructions. Orientation of inserts were checked by PCR. The sequences of the pYES2.1/V5-His-TOPO inserts for Normandy LuFAD3A and Normandy LuFAD3B are set forth as SEQ ID NOs:28 and 29. The sequences of the inserts for Solin LuFAD3A and Solin LuFAD3B are set forth as SEQ ID NOs:30 and 31.

Example 7

Expression in Yeast

Precultures were grown at 30° C. overnight in minimal media supplemented with 2% glucose and lacking uracil. Precultures were washed and used to inoculate 20 mL of induction media (mimimal media lacking uracil and supplemented with 2% galactose and 1% raffinose) to an $OD_{600}$ of 0.5. Cultures were induced for 6 hours at 20° C., then supplemented with 150 µM linoleic acid ($18:2^{\Delta9,12}$), and grown at 20° C. for 3 days.

Fatty Acid Analysis

Yeast cells were pelleted by centrifugation, washed once with induction media and once with water, suspended in 2 mL of 3N HCl and incubated at 80° C. for 30 min. After the addition of 1 mL of 9% NaCl, the sample was extracted with 2.5 mL of hexane. The hexane extract was dried and resuspended in 200 µL of hexane, and analyzed on a Hewlett Packard 5890A Gas Chromatograph equipped with a DB-23 column (30 m×250 µm×0.23 µm). The temperature was programmed to hold at 160° C. for 1 min, increase to 240° C. at 4° C./min, and hold for 10 min. Results are summarized in FIGS. 1 and 2 which shows that 18:2(9,12) (linoleic acid) was desaturated to 18:3(9,12,15) (linolenic acid) in cultures containing LuFAD3A or LuFAD3B from Normandy. However, cultures containing either LuFAD3A or LuFAD3B from Solin showed no evidence of desaturation of linoleic acid.

Example 8

Markers for LuFAD3A and LuFAD3B

Genomic DNA was isolated from young leaves and cotyledons of Solin and Normandy using a DNAesy maxi kit according to the manufacturers' instructions. Each PCR reaction contained 50 pmol of each primer, 2.5 uL MgCl (50 mM) 5 uL Invitrogen 10×PCR Buffer (200 mM Tris-HCl, 500 mM KCl) 1 uL Invitrogen Taq DNA polymerase (5 U/µL), 1 µL dNTPs (each at 10 mM) and approximately 100 ng genomic DNA in a volume of 50 □L. The PCR program consisted of a 4 min denaturation cycle at 94° C., followed by 25 cycles of 94° C. for 45 s, 61° C. for 30 s and 72° C. for 2 min, and a final 10 min extension at 72° C. Three separate reactions including Solin, Normandy, or a 1:1 mix of Solin and Normandy genomic DNA, were performed with each primer set. The primer set MutAF2/MutAR2 was used to distinguish wild-type versus mutant LuFAD3A genes, while Lu15bFLF/NcDNAbEndR was used to distinguish LuFAD3B genes. The sequences of MutAF2 and MutAR2 are set forth as SEQ ID NOs:32 and 33. Two identical 50 µL PCR reactions were combined and purified with a Qiagen QIAquick PCR purification column according to the manufacturers' instructions and were eluted in 50 µL of water. Twenty µL of elutant was digested with 20-30 units of the appropriate enzyme (PvuI for LuFAD3A, BsaJI for LuFAD3B reactions) in a total volume of 30 µL for 3 hours. Digests were run on 1.5-2.0% agarose gels (FIG. 3).

Figure 3:
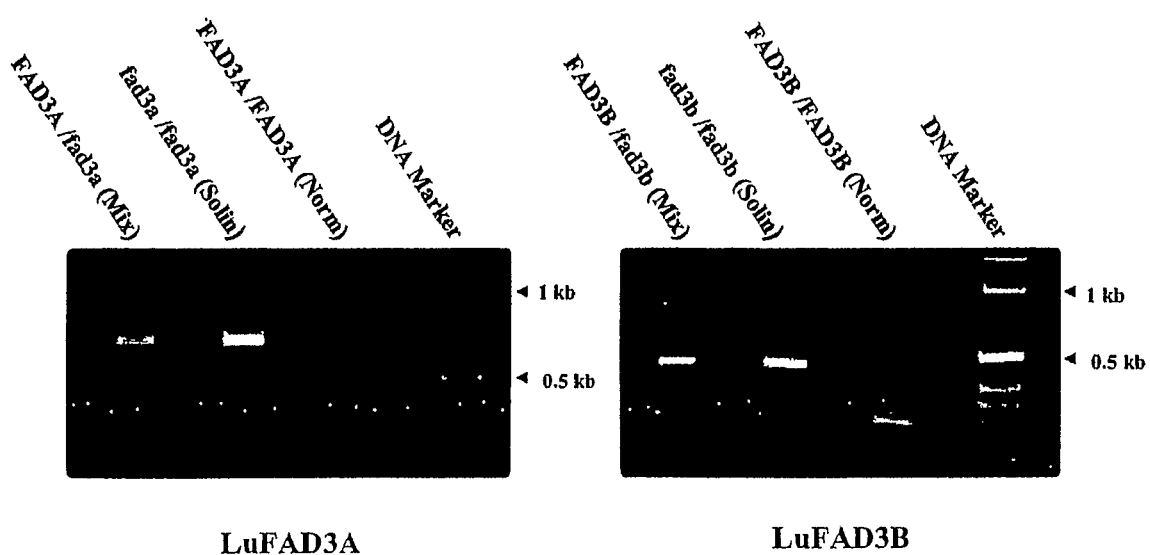
FIG. 3 shows markers distinguishing wild-type and mutant LuFADA and LuFADB genes. For LuFAD3A genes, genomic DNA was amplified using the primer set MutAF2/MutAR2 and the amplification product was digested with PvuI. Primers Lu15bFLF/NcDNAbEndR and restriction enzyme BsaJI was used for LuFAD3B genes. Digested PCR reactions were run on 1.5-2.0% agarose gels. The markers for both LuFAD3A and LuFAD3B were capable of distinguishing wild-type homozygous, mutated homozygous, and heterozygous (mix) samples.

The markers for both LuFAD3A and LuFAD3B were capable of distinguishing wild-type homozygous, mutated homozygous, and heterozygous (mix) samples (FIG. 3).

Example 9

Isolation of Promoter Regions

The primers Lu15ProF and Lu15ProR were designed based on the previously patented LuFAD3A promoter (Qiu et al. (2003)) and cover 1000 bp upstream of the LuFAD3A start codon. The sequences of Lu15ProF and Lu15ProR are set forth as SEQ ID NOs:34 and 35. These primers were used to isolate promoter regions from genomic DNA of both Normandy and Solin. Genomic DNA was isolated from young leaves and cotyledons using a DNAesy maxi kit according to the manufacturer's instructions. PCR reactions included 50 pmol of each primer, 5 µL Stratagene PfuUltra 10× Reaction Buffer, 1.0 µL dNTP mix (each at 10 mM), 2.5 U Stratagene PfuUltra DNA Polymerase and approximately 100 ng of either Solin or Normandy genomic DNA in a volume of 50 µL. The PCR program consisted of a 4 min denaturation cycle at 94° C., followed by 25 cycles of 94° C. for 45 s, 58° C. for 30 s and 72° C. for 2 min, and a final 10 min extension at 72° C. Amplification products were cloned into PCR4 and sequenced. The cloned amplification products from Normandy included two sequences, one of which was identical to the previously patented FAD3A promoter. While the second amplification product had regions of homology to the LuFAD3A promoter, it was not identical, suggesting it represented the LuFAD3B promoter region. This sequence is set forth as SEQ ID NO:7.

To confirm that this sequence represents the LuFAD3B promoter, the primers LuBProF (located within the LuFAD3B coding region) and LuBProR (specific to the B-promoter amplification product) were used to amplify Normandy genomic DNA using the conditions described above. The sequences of LuBProF and LuBProR are set forth as SEQ ID NOs:36 and 37. The amplification product was cloned into PCR4-TOPO and sequenced. The sequenced insert is set forth as SEQ ID NO:38. This sequence is homologous with the 5' end of the LuFAD3B gene as well as with SEQ ID NO:7, indicating that SEQ ID NO:7 represents the flax FAD3B promoter. Insert sequences of clones produced from PCR reactions using Solin as a template included a sequence representing the Solin LuFAD3A promoter and a second sequence representing the Solin LuFADB promoter. While the LuFAD3A promoter of Solin differed by one bp from that of Normandy, as described by Qiu et al (2003), the LuFAD3B promoters isolated from Normandy and Solin were identical.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule which directs gene expression in a developing plant seed, comprising the nucleotide sequence of SEQ ID NO: 7.

2. The isolated nucleic acid molecule of claim 1, wherein the developing plant seed is an oilseed crop plant seed.

3. The nucleic acid molecule of claim 2, wherein the oilseed crop plant is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacao*), and peanut (*Arachis* sp.).

4. The isolated nucleic acid molecule of claim 1, operatively linked to a gene.

5. The isolated nucleic acid molecule of claim 4, wherein the gene is involved in fatty acid biosynthesis or lipid biosynthesis.

6. The isolated nucleic acid molecule of claim 5, wherein the gene is a desaturase.

7. A vector comprising the isolated nucleic acid molecule of claim 1.

8. A host cell transformed with the vector of claim 7.

9. A method of producing a polypeptide comprising culturing the host cell of claim 8 in an appropriate culture medium to, thereby, produce the polypeptide.

10. A method of transforming a plant cell comprising preparing a nucleic acid construct comprising the isolated nucleic acid molecule of claim 1, and introducing said nucleic acid construct into the plant cell.

11. A transgenic plant prepared by the method of claim 10.

12. The transgenic plant of claim 11, wherein the plant is an oilseed crop plant.

13. The transgenic plant of claim 12, wherein the oilseed crop plant is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), and peanut (*Arachis* sp.).

14. A transgenic seed having a transgene integrated into the genome of the seed, wherein the transgene comprises the isolated nucleic acid molecule of claim 1.

15. The transgenic seed of claim 14, wherein the seed is an oilseed plant seed.

16. The transgenic seed of claim 15, wherein the oilseed plant seed is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), and peanut (*Arachis* sp.).

17. The method of claim 10, wherein the isolated nucleic acid molecule is operatively linked to a gene.

18. The method of claim 17, wherein the gene is involved in fatty acid biosynthesis or lipid biosynthesis.

19. The method of claim 18, wherein the gene is a desaturase.

20. The transgenic seed of claim 14, wherein the isolated nucleic acid molecule is operatively linked to a gene.

21. The transgenic seed of claim 20, wherein the gene is involved in fatty acid biosynthesis or lipid biosynthesis.

22. The transgenic seed of claim 21, wherein the gene is a desaturase.

* * * * *